United States Patent

Hayashi et al.

[11] 3,931,296
[45] Jan. 6, 1976

[54] TRANS-Δ²-PROSTAGLANDINS

[76] Inventors: Masaki Hayashi, 32-408 Nanpeidai; Hirohisa Wakatsuka, 1319 Makita-cho; Seiji Kori, 1-281 Higashishiroyama-cho, all of Takatsuki, Japan

[22] Filed: Dec. 21, 1973

[21] Appl. No.: 427,403

[30] Foreign Application Priority Data
Dec. 29, 1972 Japan................................. 48-2427
Nov. 2, 1973 Japan............................. 48-122796

[52] U.S. Cl....... 260/514 D; 260/290 R; 260/209 R; 260/57; 260/58; 260/59; 260/468 D; 260/617 R; 424/305; 424/317
[51] Int. Cl.²................... C07C 61/38; C07C 69/74
[58] Field of Search......... 260/468 D, 514 D, 209 R

[56] References Cited
OTHER PUBLICATIONS
Beerthuis et al., Rec. Trav. Chim. Pay Bus., 90,943 (1971).

*Primary Examiner*—Robert Gerstl
*Attorney, Agent, or Firm*—Albert H. Graddis; Frank S. Chow

[57] ABSTRACT

New process for the preparation of trans-Δ²-prostaglandins of the formula

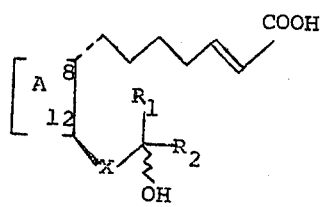

(wherein A represents a grouping of the PGE, PGF or PGA type, X represents —CH₂CH₂— or trans —CH=CH—, R₁ represents an alkyl radical of 1 to 10 carbon atoms or an alkyl radical of 1 to 6 carbon atoms carrying a phenyl substituent or a cycloalkyl substituent of 5 to 7 carbon atoms, R₂ represents a hydrogen atom or an alkyl radical of 1 to 4 carbon atoms) and alkyl esters thereof having 1 to 10 carbon atoms in the chain, which comprises reacting a cyclopentane derivative of the formula:

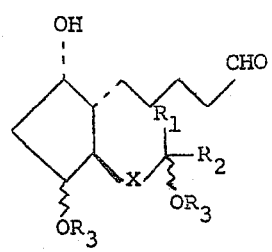

(where R₃ represents a 2-tetrahydropyranyl group unsubstituted or substituted by at least one alkyl radical, or a 1-ethoxyethyl group) with an alkyl phosphonate of the general formula:

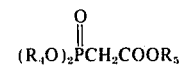

(wherein R₄ represents a methyl or ethyl radical, and R₅ represents an alkyl radical of 1 to 10 carbon atoms), optionally hydrolyzing the resulting trans-Δ²-prostaglandin ester of the general formula:

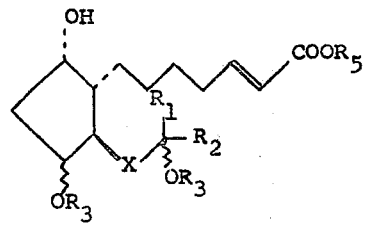

to the corresponding acid, optionally converting the 9α-hydroxy radical in the ester or acid product to an oxo group, and hydrolyzing the tetrahydropyranyloxy or ethoxyethoxy groups in the resulting trans-Δ²-prostaglandin compound of the formula:

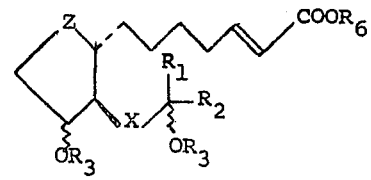

(wherein R₆ represents a hydrogen atom or an alkyl radical of 1 to 10 carbon atoms, Z represents

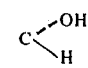

or C=O) to hydroxy radicals to obtain a trans-Δ²-PGF or trans-Δ²-PGE compound of the formula:

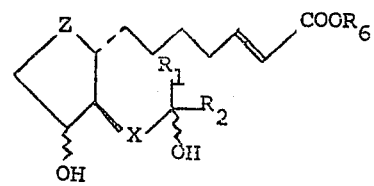

and, if desired, converting the PGE alicyclic ring (Z represents C=O) into that of a PGA compound.

The trans-Δ²-prostaglandin products, which are new compounds except for trans-Δ²-PGE₁, possess typical pharmacological properties of the 'natural' prostaglandins.

11 Claims, No Drawings

TRANS-Δ²-PROSTAGLANDINS

THIS INVENTION relates to a new process for the preparation of prostaglandin analogues, and to new prostaglandin analogues and compositions containing them.

Prostaglandins are derivatives of prostanoic acid which has the following formula:

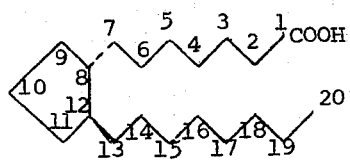

I

Various types of prostaglandins are known, the types depending inter alia on the structure and substituents on the alicyclic ring. For example, the alicyclic rings of prostaglandins E(PGE), F(PGF) and A(PGA) have the structures:

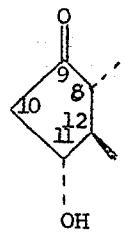

II

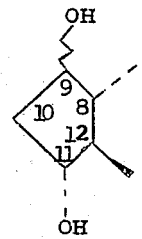

III

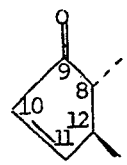

IV respectively.

Such compounds are sub-classified according to the position of double bond(s) in the side chain(s) attached to the 8- and 12-positions of the alicyclic ring. Thus PG-1 compounds have a trans-double bond between $C_{13}-C_{14}$ (trans -$\Delta^{13}$), PG-2 compounds have a cis-double bond between $C_5-C_6$ and a trans-double bond between $C_{13}-C_{14}$ (cis-$\Delta^5$, trans-$\Delta^{13}$), and PG-3 compounds have cis-double bonds between $C_5-C_6$ and $C_{17}-C_{18}$ and a trans-double bond between $C_{13}-C_{14}$ (cis-$\Delta^5$, trans-$\Delta^{13}$, cis-$\Delta^{17}$). For example, prostaglandin $F_{1\alpha}$ ($PGF_{1\alpha}$) and prostaglandin $E_1$ ($PGE_1$) are characterized by the following structures V and VI.

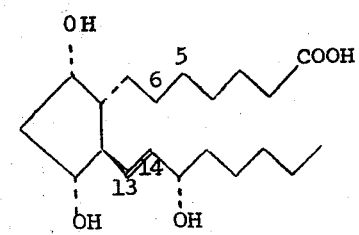

V and

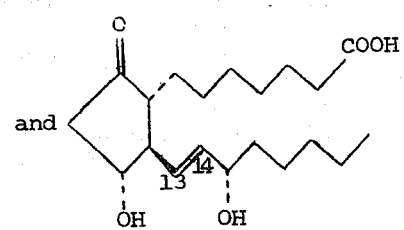

VI respectively. The structures of $PGF_{2\alpha}$ and $PGE_2$, as members of the PG-2 group, correspond to those of formulae V and VI respectively with a cis-double bond between the carbon atoms in positions 5 and 6. Compounds in which the double bond between the carbon atoms in positions 13 and 14 of members of the PG-1 group is replaced by ethylene($-CH_2CH_2-$) are known as dihydro-prostaglandins, e.g. dihydro-prostaglandin-$F_{1\alpha}$ (dihydro-$PGF_{1\alpha}$) and dihydro-prostaglandin-$E_1$ (dihydro-$PGE_1$).

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGE's and PGA's have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyper-lipemia. PGE$_1$ inhibits blood platelet aggregation and also removes the thrombus and prevents thrombosis. PGE's and PGF's have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour abortion of the placenta, and as oral contraceptives because they regulate the sexual cycle of female mammals. PGE's and PGA's have vasodilator and diuretic activities. PGE's are useful for improvement in patients suffering from cerebral vascular disease because they increase the cerebral blood flow, and are also useful in the treatment of asthmatic conditions in patients because of their bronchodilating activity.

During the past decade processes have been developed for the preparation of compounds analogous to natural prostaglandins or derivatives of prostaglandins in order to discover inter alia new products possessing the pharmacological properties of the 'natural' prostaglandins or one or more of such properties to an enhanced degree. It has been found that small changes or chemical structure from the 'natural' prostaglandins can considerably alter the pharmacological properties of the prostaglandins and can, in numerous instances, destroy therapeutic utility.

A process is known for the preparation of a prostaglandin analogous to PGE$_1$ in which there is a trans double bond between C$_2$-C$_3$, i.e. trans-$\Delta^2$-PGE$_1$, of the formula:

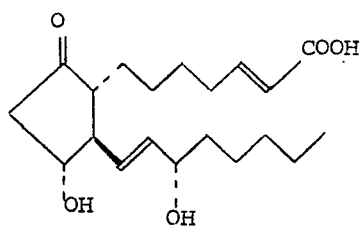

VII

The process, which is described by Van Dorp in Annals New York Academy of Sciences, 180, 185 (1971), is based on a biosynthetic reaction involving incubating sheep seminal vesicular glands with an unsaturated fatty acid as substrate, according to the reaction scheme:

However, this process is difficult and expensive to carry out on a large scale due to the complicated synthesis of the unsaturated fatty acid and the use of expensive materials of animal origin of difficult availability.

As a result of research and experimentation a new process has been evolved for the preparation of trans-$\Delta^2$-PGE$_1$, and of other prostaglandins having a trans C$_2$-C$_3$ double bond which possess the pharmacological properties of the natural prostaglandins to the same extent or to an enhanced degree, which process avoids the use of expensive materials derived from sheep and employs readily obtainable starting materials.

The present invention is concerned with a new chemical process for the preparation of trans-$\Delta^2$-prostaglandin analogues of the general formula:

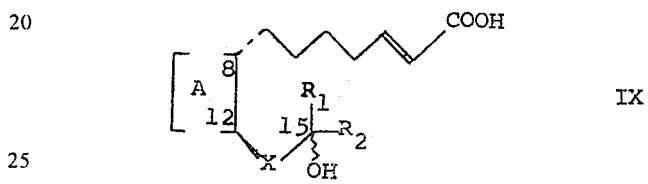

IX (wherein A represents a grouping of formula IV as indicated above or a grouping of the formula:

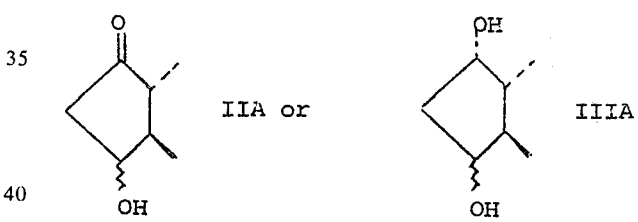

IIA or IIIA

X represents —CH$_2$CH$_2$— or trans —CH=CH—, R$_1$ represents a straight- or branched-chain alkyl radical containing from 1 to 10 carbon atoms or a straight- or branched-chain alkyl radical containing from 1 to 6 carbon atoms carrying a phenyl substituent or a cycloalkyl substituent of 5 to 7 carbon atoms, R$_2$ represents a hydrogen atom or a straight- or branched-chain alkyl radical containing from 1 to 4 carbon atoms, and $\sim$ indicates attachment of the hydroxy radical to the carbon atom in alpha or beta configuration) and alkyl esters thereof having 1 to 10 carbon atoms in a straight- or branched-chain, and cyclodextrin clathrates of such

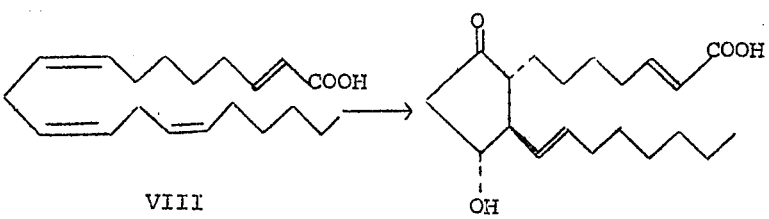

VIII acids and esters, and non-toxic (e.g. sodium) salts of the acids of formula IX.

The present invention is concerned with all compounds of general formula IX in the 'natural' form or its enantiomeric form, or mixtures thereof, more particularly the racemic form consisting of equimolecular mixtures of natural and its enantiomeric form.

As will be apparent to those skilled in the art, the compounds depicted in general formula IX have at least three centres of chirality, these three centres of chirality being at the alicyclic ring carbon atoms in the positions of group A identified as 8 to 12 and at the C-15 carbon atom which has attached to it a hydroxy radical. Still further centres of chirality occur when the alicyclic group A carries a hydroxy radical on the carbon atom in position 11 (i.e. when the ring is that of formula IIA) or hydroxy radicals in positions 9 and 11 (i.e. when the ring is that of formula IIIA). The presence of chirality leads, as is well known, to the existence of isomerism. However, the compounds of general formula IX all have such a configuration that the side chains attached to the ring carbon atoms in the positions identified as 8 and 12 are trans with respect to each other. Accordingly, all isomers of general formula IX, and mixtures thereof, which have those side-chains attached to the ring carbon atoms in positions 8 and 12 in the trans configuration and have a hydroxy radical in the 15-position are to be considered within the scope of general formula IX.

According to the present invention, the trans-$\Delta^2$-prostaglandins of general formula IX are prepared by the process which comprises reacting a cyclopentane derivative of the general formula:

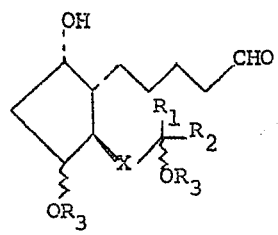

X (wherein $R_3$ represents a 2-tetrahydropyranyl group unsubstituted or substituted by at least one alkyl radical, or a 1-ethoxyethyl group, X, $R_1$ and $R_2$ are as hereinbefore defined, and ⋀ indicates attachment of the $OR_3$ groups to the carbon atom in alpha or beta configuration) with an alkyl phosphonate of the general formula:

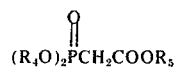

XI (wherein $R_4$ represents a methyl or ethyl radical, and $R_5$ represents a straight- or branched-chain alkyl radical containing from 1 to 10 carbon atoms), optionally hydrolyzing the resulting trans-$\Delta^2$-prostaglandin ester of the general formula:

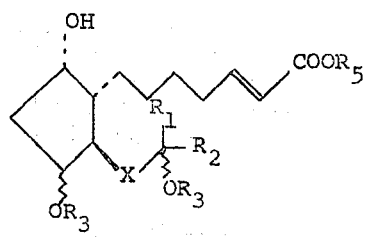

XII (wherein X, $R_1$, $R_2$, $R_3$, $R_5$ and ⋀ have the meanings hereinbefore specified) to the corresponding acid of the general formula:

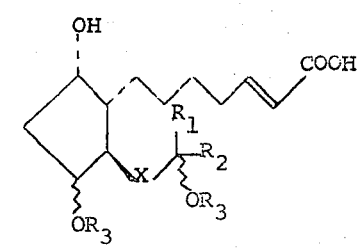

XIII (wherein X, $R_1$, $R_2$, $R_3$ and ⋀ have the meanings hereinbefore specified), optionally converting by methods known per se the 9α-hydroxy radical in the compounds of general formulae XII and XIII to an oxo group, and hydrolyzing the tetrahydropyranyloxy or ethoxyethoxy groups in the resulting trans-$\Delta^2$-prostaglandin compound of the general formula:

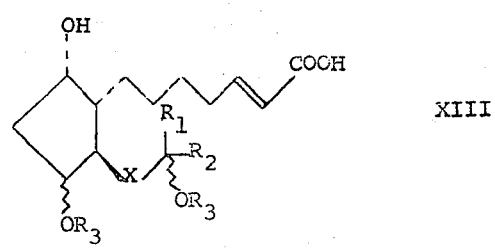

XIV (wherein $R_6$ represents a hydrogen atom or a straight- or branched-chain alkyl radical containing from 1 to 10 carbon atoms, Z represents

or C=O, and X, $R_1$, $R_2$, $R_3$ and ⋀ have the meanings hereinbefore specified) to hydroxy radicals to obtain a PGF or PGE compound of the general formula:

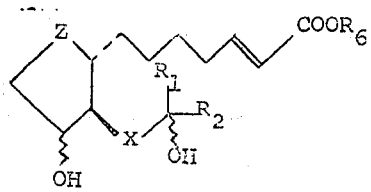

XV (wherein X, $R_1$, $R_2$, Z, $R_6$ and ⋀ have the meanings hereinbefore specified) and, if desired, converting by methods known per se the PGE alicyclic ring (Z represents C=O) into that of a PGA compound. By the term "methods known per se" as used in this specification is meant methods heretofore used or described in the chemical literature.

The intermediate compounds of general formula XIV, which are new compounds and as such constitute a feature of the invention, may thus be converted into trans-$\Delta^2$-prostaglandins of general formula IX, or alkyl esters thereof, by the reactions depicted schematically below:

for example by treatment of the ester in an inert organic solvent (e.g. tetrahydrofuran) with an aqueous solution of sodium or potassium hydroxide or carbonate.

The tetrahydropyranyloxy and ethoxyethoxy groups ($\sim$OR$_3$) in the intermediate compounds of general

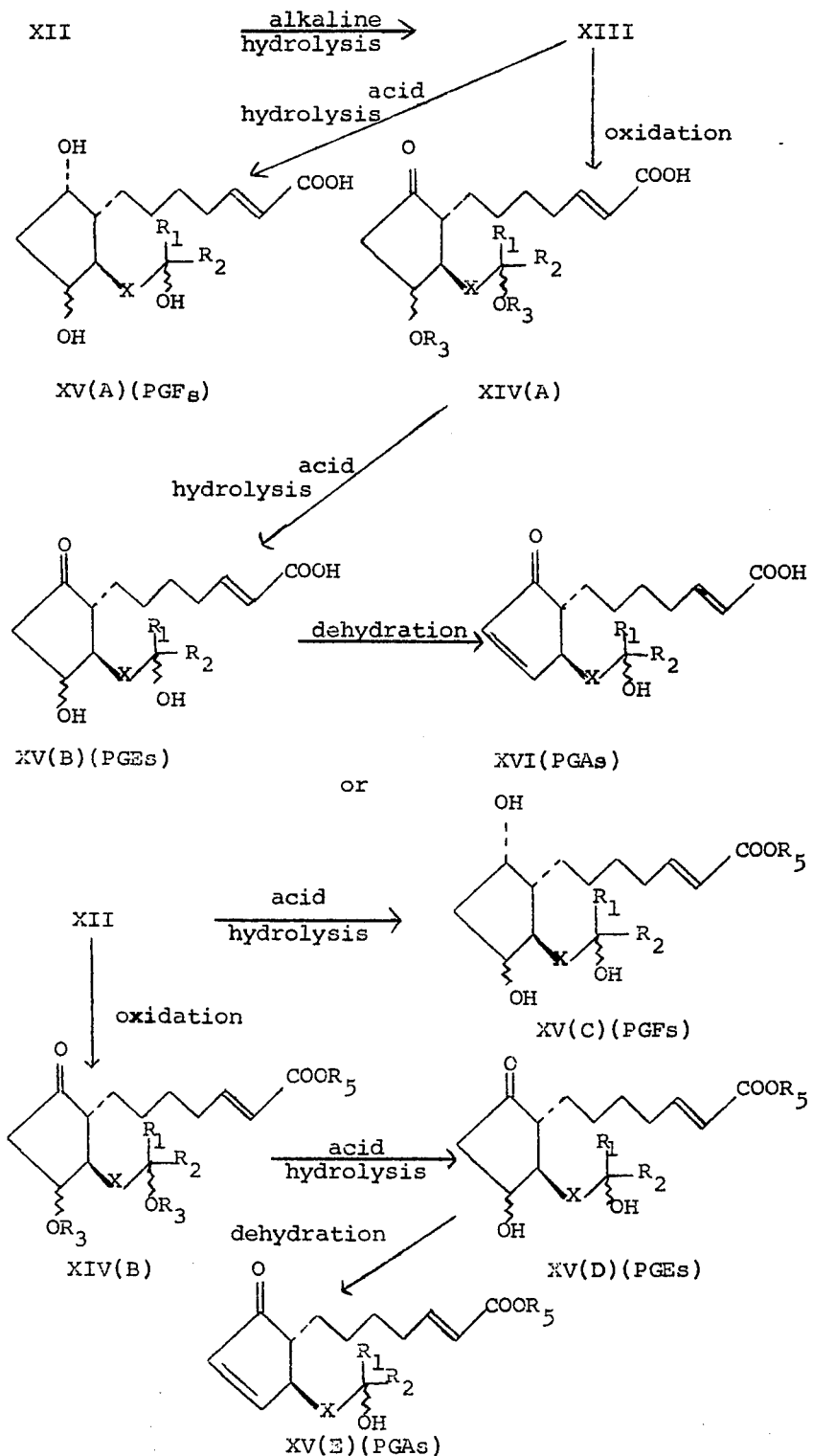

wherein the various symbols and $\sim$ are as hereinbefore defined.

The hydrolysis of the alkyl esters of general formula XII to the corresponding acids of general formula XIII may be carried out according to methods known per se, formula XII, XIII and XIV [including XIV(A) and (B)] may be converted into hydroxy radicals by mild hydrolysis with an aqueous solution of an organic acid, e.g. acetic acid, or with a dilute inorganic acid, e.g. dilute hydrochloric acid. Advantageously an organic solvent miscible with water, such as tetrahydrofuran or an alcohol, is employed as starting acids of general formulae XV [including XV(A) and (B)] are practically insoluble in water. The treatment of the compounds of general formulae XII, XIII and XIV may be carried out at a temperature ranging from ambient temperature to 60°C. (preferably at a temperature below 45°C.) with an acid mixture, such as a mixture of acetic acid, water and tetrahydrofuran, or a mixture of hydrochloric acid with tetrahydrofuran or methanol.

The PGF alicyclic ring in the compounds of general formulae XII and XIII can be converted into a PGE ring [cf. formulae XIV(A) and (B)] by methods known per se for the conversion of a hydroxy group in the 9-position of a prostaglandin to an oxo radical, for example by means of a chromic acid solution (e.g. obtained from chromium trioxide, manganese sulphate, sulphuric acid and water) or Jones' reagent.

The PGE compounds of general formula XV [Z represents C=O, cf. formula XV(B) and (D)] can be converted into corresponding PGA compounds by methods known per se, for example by subjecting the PGE's to dehydration using an aqueous solution of an organic or inorganic acid having a higher concentration than that employed for hydrolysis of compounds of general formulae XII, XIII and XIV, e.g. acetic acid for 1N hydrochloric acid, and heating at a temperature of 30°–60°C.

The reaction between the cyclopentane derivatives of general formula X and the alkyl phosphonates of general formula XI (in the form of a sodio derivative formed, for example, by reaction of sodium hydride with the alkyl phosphonate in an inert organic medium) is carried out under the normal conditions utilized for effecting a Wittig reaction, e.g. in an inert organic solvent at a temperature not exceeding 30°C. The reaction is preferably carried out by suspending a strong base, such as sodium hydride, in an inert organic medium (e.g. tetrahydrofuran or dimethoxymethane), adding the alkyl phosphonate thereby to form its sodio derivative with evolution of hydrogen, and adding to the resulting solution of the sodium alkyl phosphonate the cyclopentane derivative of general formula X. By the Wittig reaction a trans-$\Delta^2$ double bond is formed stereospecifically and a compound of general XII is obtained.

The cyclopentane derivatives of general formula X, which are new compounds and as such constitute a feature of the invention, can be prepared by the series of reactions depicted schematically below:

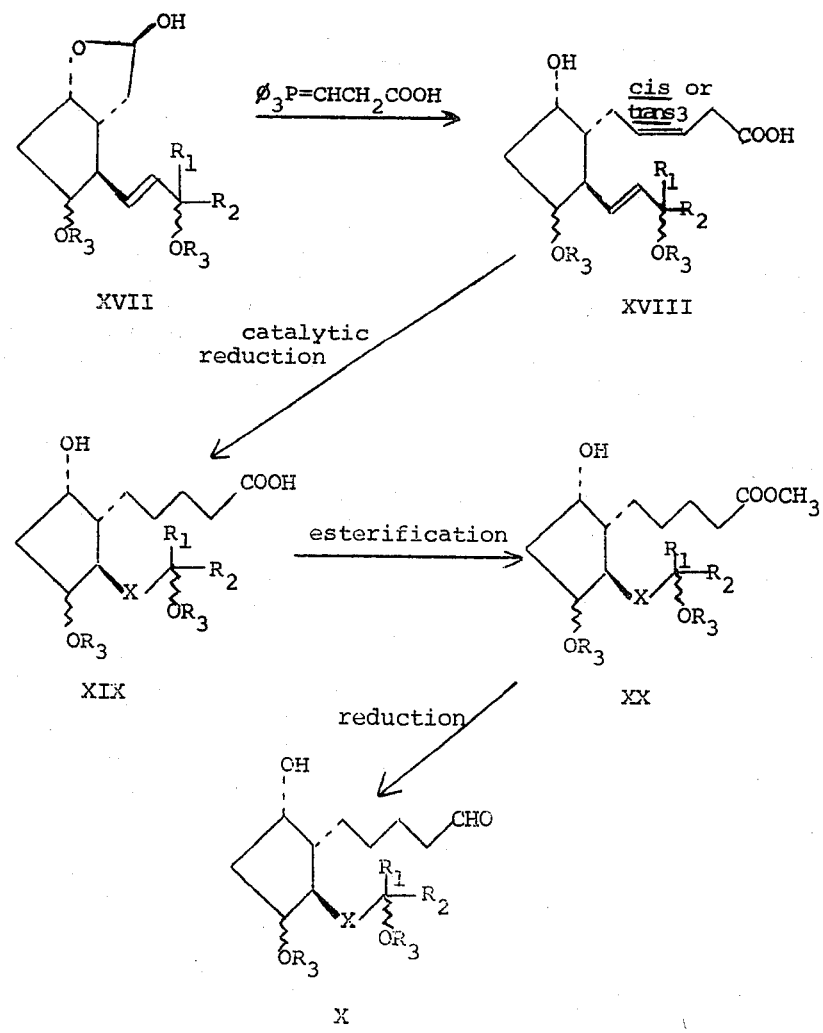

wherein $\phi$ represents the phenyl radical, and the other symbols and ∿ have the meanings hereinbefore specified.

The reaction between the bicyclo-octanes of general formula XVII and 2-carboxyethylidenetriphenylphosphorane [obtained by the reaction of sodiomethylsulphinylcarbanide with 2-carboxyethyltriphenylphosphonium bromide, itself prepared from 3-bromopripionic acid and triphenylphosphine] is carried out under the normal conditions utilized for effecting the Wittig reaction, e.g. in an inert solvent at or about ambient temperature. The reaction is preferably carried out in dimethylsulphoxide because the phosphorane compound is practically insoluble in other solvents, e.g. tetrahydrofuran. For the better performance of the Wittig reaction more than two molecular equivalents of the phosphorane compound are required for each mole of the bicyclo-octane reactant. The reaction is generally effected at a temperature of 0°–40°C., preferably at 20°–30°C., and is usually complete after about 1 to five hours at laboratory temperature. The acid product of formula XVIII (a mixture of cis-$\Delta^3$- and trans-$\Delta^3$-forms) may be extracted from the reaction mixture by conventional procedures and further purified by column chromatography on silica gel.

The catalytic hydrogenation of the compounds of general formula XVIII can be carried out as follows:

The hydrogenation catalyst, i.e., a catalyst usually used for the hydrogenation of double bonds such as various forms of platinum, palladium or nickel, is suspended in an adequate amount of a solvent acting as reaction medium, and the suspension placed in an apparatus appropriate for a catalytic reduction process. The air inside the apparatus is replaced by hydrogen, and a solution of the cyclopentane compound in a suitable inert solvent (for example methanol, ethanol, water, dioxan or acetic acid, or a mixture of two or more of them) is added to the suspension of the catalyst. The reaction takes place at about 0°C. to 50°C. until one or two times the molar quantity of hydrogen has been consumed according to whether or not it is desired to reduce the trans double bond adjacent to the carbon atom carrying the $OR_3$ group in the starting material of formula XVIII as well as the cis or trans double bond in β-position to the carboxy radical, for example for a period of 0.5 to 8 hours. After completion of the reaction, the catalyst is removed by means of a filter, and the filtrate concentrated. If necessary, the residue is purified by column chromatography using silica gel or silica gel impregnated with silver nitrate.

The trans double bond adjacent to the carbon atom carrying the $OR_3$ group is difficult to hydrogenate due to steric hindrance by the tetrahydropyranyloxy or ethoxyethoxy group $OR_3$. The double bond between positions 3- and 4 can be reduced by appropriate selection of the catalyst (palladium is satisfactory), the reaction temperature and time.

Esterification of the acids of general formula XIX to the methyl esters of general formula XX can be effected by methods known per se for converting the carboxy radical to a methoxycarbonyl group, for example by reaction with diazomethane in an inert organic solvent, such as diethyl ether, under mild conditions.

The methyl esters of general formula XX can be reduced to the corresponding aldehydes of general formula X by methods known per se for converting a methoxycarbonyl group to the formyl radical (—CHO), for example by reduction of the methyl esters with diisobutylaluminiumhydride in an inert organic solvent, e.g. toluene, preferably at a low temperature.

The alkyl phosphonate starting materials of general formula XI can be synthesized by the procedure described by G. M. Kosolapoff, J. Amer. Chem. Soc. 68, 1103 (1946), according to the reaction sequence:

wherein $R_4$ and $R_5$ are as hereinbefore defined.

The bicyclo-octane compounds of general formula XVII can be prepared using initially 2-oxa-3-oxo-6-syn-formyl-7-anti-acetoxy-cis-bicyclo[3,3,0]-octane [E. J. Corey et al, J. Amer. Chem. Soc. 92, 397 (1970)]and applying thereto known procedures [see, for example, J. Amer. Chem. Soc. 91, 5675 (1969) and French Patent No. 7215314 (Publication No. 2134673)].

Trans-$\Delta^2$-prostaglandins of general formula IX obtained by the process of the present invention can be converted into salts or esters, preferably alkyl esters containing 1 to 10 carbon atoms.

The salts may be prepared from the compounds of general formula IX by methods known per se, for example by reaction of stoichiometric quantities of acids of general formula IX and the appropriate base, e.g. an alkali metal hydroxide or carbonate, ammonium hydroxide, ammonia or an amine, in a suitable solvent. The salts may be isolated by lyophilisation of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the trans-$\Delta^2$-prostaglandins of general formula IX are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

Esters of the trans-$\Delta^2$-prostaglandins of general formula IX can be obtained by reaction of the acids with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. Belgian Patents Nos. 775106 and 776294).

The trans-$\Delta^2$-prostaglandins of general formula IX can also be converted into prostaglandin alcohols, i.e. compounds in which the carboxy radical is replaced by the hydroxymethylene (i.e. —CH$_2$OH) group, of the general formula:

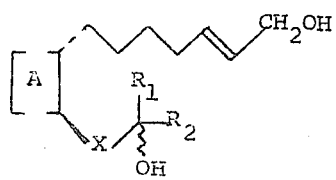

wherein the various symbols and ⋎⋎ have the meanings hereinbefore specified.

The trans-Δ²-prostaglandin alcohols of general formula XXI can be prepared from the acids of general formula IX by application of the method described by Pike, Lincoln and Schneider in J. Org. Chem. 34, 3552–3557 (1969), for example by converting the acids of general formula IX into their methyl esters and then the esters into oximes, and reducing the oximes with lithium aluminum hydride to form oxime alcohols, and hydrolyzing them with, for example, acetic acid. Trans-Δ²-PGF alcohols can also be obtained directly by reducing trans-Δ²-PGF compounds of general formula IX, or methyl esters thereof, with lithium aluminum hydride. The alcohol derivatives of prostaglandins of general formula XXI possess pharmacological properties similar to the acids of general formula IX from which they are derived.

The prostaglandin compounds of general formula IX and esters thereof, and corresponding alcohols of general formula XXI may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70°C. during the preparation of the cyclodextrin clathrates. α, β or γ-Cyclodextrins or mixtures thereof may be used in the preparation of the cyclodextrin clathrates. Conversion into their cyclodextrin clathrates serves to increase the stability of the prostaglandin compounds.

Prostaglandin compounds obtained by the process of the present invention and esters and alcohol derivatives thereof, and their cyclodextrin clathrates, and non-toxic salts possess the valuable pharmacological properties typical of prostaglandins in a selective fashion including, in particular, hypotensive activity, inhibitory activity on blood platelet aggregation, inhibitory activity on gastric acid secretion and gastric ulceration and bronchodilator activity and are useful in the treatment of hypertension, in the treatment of disorders of the peripheral circulation, in the prevention and treatment of cerebral thrombosis and myocardial infarction, in the treatment of gastric ulceration and in the treatment of asthma, 16(R)-methyl-trans-Δ²-PGE₁ being particularly preferred in respect of these properties. For example, in laboratory screening tests, the compound 16(R)-methyl-trans-Δ²-PGE₁ produces:

a. a 26 mm.Hg fall for 11 minutes and a 66 mm.Hg fall for 18 minutes in the blood-pressure of the allobarbital-anaesthetized dog by intravenous administration at doses of 0.05 and 0.20 μg./kg. animal body weight respectively and is 9.5 times as potent as PGE₁ in this respect;

b. 50% inhibition of adenosine diphosphate-induced blood platelet aggregation in platelet-rich plasma of rabbits at a dose of $3.1 \times 10^{-2}$ μg./ml. in comparison with controls, the corresponding dose for PGE₁ being $8.8 \times 10^{-2}$ μg./ml.;

c. an increase in gastric acid pH from 2.0–2.5 to at least 4.0 in 50% of pentagastrin-treated rats when perfused into the stomach at a rate of 0.12 (confidence limit 0.076–0.190) μg./animal/minute;

d. 23.02% and 31.14% inhibitions of stress ulceration in rats [produced according to the method of Takagi and Okabe — Jap. J. Pharmac. 18, 9–18 (1968)] by oral administration at doses of 2 and 10 μg./kg. animal body weight respectively, and e. 55.9% and 62.0% inhibitions by intravenous administration at doses of 0.05 and 0.10 μg./kg. animal body weight, respectively, of the increase in resistance in the respiratory tract induced by the administration of histamine to guinea-pigs, as determined by the method of Konzett and Rossler, Arch. exp. Path. Pharmak., 195, 71–74 (1940).

Moreover, when trans-Δ²-PGE₁, trans-Δ²-PGA₁, trans-Δ²-dihydro-PGE₁ are administered intravenously to the allobarbital-anaesthetised dog at doses of 1 μg./kg. animal body weight, 0.2 μg./kg. animal body weight and 1 μg./kg. animal body weight respectively, the compounds produce falls of 18 mm.Hg, 20 mm.Hg and 18 mm.Hg respectively in blood-pressure. Trans-Δ²-PGE₁ also inhibits adenosine diphosphate induced blood platelet aggregation in platelet-rich plasma of rats and also in human blood, and with rat blood showed itself to have an activity 2.95 times that of PGE₁ and with human blood 7.15 times the activity of PGE₁.

The trans-Δ²-prostaglandins of general formula IX (with the exception of trans-Δ²-PGE₁) are new compounds and as such they and their esters and alcohol derivatives thereof conforming to general formula XXI, and cyclodextrin clathrates of such acids, esters and alcohol derivatives, and salts of the acids of general formula IX, constitute a particularly important aspect of the invention. Of particular interest are those compounds of general formula IX wherein the grouping

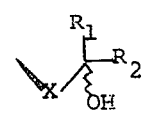

is of the general formula:

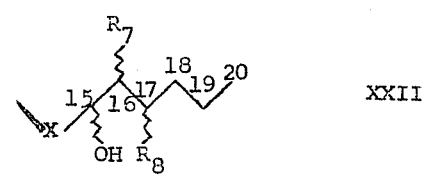

XXII wherein X and ∿ have the meanings hereinbefore specified, and R₇ and R₈ each represent a hydrogen atom or a methyl or ethyl radical, or such a grouping in which R₇ and R₈ represent hydrogen atoms and the carbon atom in the 15-, 18- or 19-position carries a methyl radical, or the carbon atoms in the 15- and 16-positions each carry a methyl radical, or a grouping of the general formula:

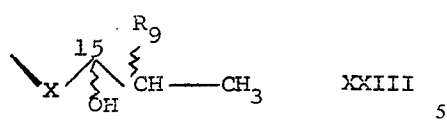

XXIII wherein X and ⋁⋀ are as hereinbefore specified, and $R_9$ represents a phenyl, cyclohexyl or cyclopentyl radical.

Of outstanding importance are trans-$\Delta^2$-PGE$_1$, trans-$\Delta^2$-PGA$_1$, trans-$\Delta^2$-PGF$_{1\alpha}$, trans-$\Delta^2$-13,14-dihydro-PGE$_1$, trans-$\Delta^2$-13,14-dihydro-PGA$_1$, trans-$\Delta^2$-13,14-dihydro-PGF$_{1\alpha}$, and corresponding 15-methyl, 16-methyl, 17-methyl, 18-methyl, 19-methyl, 15,16-dimethyl, 16,17-dimethyl, 16-ethyl and 17-ethyl compounds, and corresponding 16-phenyl-ω-trinor and 16-cyclohexyl-ω-trinor analogues thereof. It is to be understood that in the aforesaid compounds the methyl, ethyl, phenyl and cyclohexyl substituents may have the R -or S-configuration, or be a mixture of R- and S-configurations, preferably a racemic mixture.

The following Reference Examples and Examples illustrate the process of the present invention and products thereof.

REFERENCE EXAMPLE 1

Synthesis of 2-carboxyethyl-triphenylphosphonium bromide

A solution of 90 g. (0.343 mole) of triphenylphosphine and 50 g. (0.326 mole) of 3-bromopropionic acid in 550 ml. of acetonitrile was refluxed for two days. The reaction mixture was then distilled under reduced pressure to remove acetonitrile, and the residue was stirred well together with diethyl ether, and then the upper ethereal layer removed by decantation. The operation was repeated twice to form the crystalline product, which was recrystallised from acetonitrile; yield of the title compound: 115 g, m.p. 195°–198°C. Infra-red (hereinafter abbreviated to IR) absorption spectrum (potassium bromide tablet): 2880, 1740, 1434, 1382, 1322, 1230, 1105, 745, 690, 520 and 505 cm$^{-1}$.

REFERENCE EXAMPLE 2

Synthesis of 9α-hydroxy-11α,15α-bis(2-tetrahydropyranyloxy)-α-dinor-prost-trans-13-enoic acid A solution of 88 g. (0.212 mole) of 2-carboxyethyl-triphenylphosphonium bromide (prepared as described in Reference Example 1) in 170 ml. of dimethylsulphoxide was mixed with 202 ml. of dimethylsulphoxide containing 2 moles of sodiomethylsulphinyl carbanide (0.40 mole as sodiomethylsulphinyl carbanide) whilst maintaining the temperature at 25°C. To the resulting red mixture was added 150 ml. of a solution containing 31 g. (0.0706 mole) of 2-oxa-3-hydroxy-6-syn-(3α-2'-tetrahydropyranyloxy-oct-trans-1-enyl)-7-anti-(2-tetrahydropyranyloxy)-cis-bicyclo[3,3,0]octane [prepared as described in J. Amer. Chem. Soc. 92, 397 (1970)] in 150 ml. of dimethylsulphoxide. The resulting mixture was stirred for 2 hours at 25°C., and then poured into 3 liters of ice-water, 350 ml. of diethyl ether and 5 g. of potassium carbonate, and extracted with 350 ml. of ethyl acetate. The aqueous layer was extracted three times with 700 ml. of a diethyl ether-ethyl acetate mixture (1:1) and washed to remove the neutral substances. The aqueous layer was adjusted to pH 2 with oxalic acid and extracted 4 times with 1.4 liters of a diethyl ether-pentane mixture (1:1), and the extract was washed with water, dried and concentrated under reduced pressure. The residue was purified using silica gel column chromatography with an ethanol-benzene mixture (6~10:100) as eluent to give 9α-hydroxy-11α,15α-bis(2-tetrahydropyranyloxy)-α-dinor-prosta-cis-and trans-5, trans-13-dienoic acids as a colourless oil in a yield of 17.5 g. ( 48%).

IR absorption spectrum (liquid film): 2920, 1710, 1200, 1130, 1020, and 975 cm$^{-1}$;

nuclear magnetic resonance (hereinafter abbreviated to NMR) spectrum; (deuterochloroform — hereinafter abbreviated to CDCl$_3$-solution): δ=7.00 (2H, singlet), 5.50 (4H, multiplet), 4.68 (2H, multiplet), and 4.20 − 3.00 (9H, multiplet).

The product was dissolved in 285 ml. of methanol, mixed with 8.5 g. of 5% palladium carbonate and treated with an equimolar amount of hydrogen at room temperature. The reaction mixture was filtered with a glass filter to remove the catalyst and the filtrate concentrated under reduced pressure to yield the title compound: 14.4 g. (82% yield).

Following the above procedure but starting with a corresponding bicyclo-octane compound having a methyl substituent on the carbon atom in the 4- or 5-position of the octenyl chain, there were prepared 9α-hydroxy-11α,15α-bis(2-tetrahydropyranyloxy)-α-dinor-16-methyl-prost-trans-13-enoic acid and 9α-hydroxy-11α,15α-bis(2-tetrahydropyranyloxy)-α-dinor-17-methyl-prost-trans-13-enoic acid.

Similar products to those mentioned in this Example can be prepared from bicyclo-octane starting materials in which the tetrahydropyranyl radical is replaced by the 1-ethoxyethyl group.

REFERENCE EXAMPLE 3

Synthesis of methyl 9α-hydroxy-11α,15α-bis(2-tetrahydropyranyloxy)-α-dinor-prost-trans-13-enoate To a solution of 2.95 g. (5.94 mmole) of 9α-hydroxy-11α,15α-bis(2-tetrahydropyranloxy)-α-dinor-prost-trans-13-enoic acid (prepared as described in Reference Example 2) in 100 ml. of diethyl ether was added a newly prepared solution of diazomethane in diethyl ether until the reaction mixture became yellow. The reaction mixture was then concentrated under reduced pressure and low temperature, and the residue purified by means of silica gel column chromatography using an ethyl acetate-cyclohexane mixture (1:1) as eluent to yield 2.43 g. (80%) of the title compound as a colourless oil.

IR absorption spectrum (liquid film): 3450, 2900, 1735, 1432, 1200, 1120, 1015, and 970 cm$^{-1}$;

NMR spectrum (in CDCl$_3$): δ = 5.30 (2H, multiplet), 4.58 (2H, multiplet), 3.56 (3H, singlet), 4.10 − 3,20 (7H, multiplet);

thin layer chromatography (hereinafter abbreviated to TLC) [ethyl acetate-cyclohexane mixture 1:1)] Rf = 0.66.

Following the same procedure but starting with a corresponding α-dinor-16-methyl-prost-trans-13-enoic acid, and α-dinor-17-methyl-prost-trans-13-enoic acid, there were obtained as products methyl 9α-hydroxy-11α,15α-bis(2-tetrahydropyranyloxy)-α-dinor-16-methyl-prost-trans-13-enoate and methyl 9α-hydroxy-11α,15α-bis(2-tetrahydropyranyloxy)-α-dinor-17-methyl-prost-trans-13-enoate.

Similar products to those mentioned in this Reference Example can be obtained when the tetrahydropyranyl radical in the α-dinor-prost-trans-13-enoic acid starting material is replaced by the 1-ethoxyethyl group.

REFERENCE EXAMPLE 4

Synthesis of 9α-hydroxy-11α,15α-bis(2-tetrahydropyranyloxy)-α-dinor-prost-trans-13-enaldehyde A solution of 1.827 g. (3.58 mmole) of the title methyl ester product of Reference Example 3 in 54 ml. of toluene was cooled to −65°C., mixed with 8.14 ml. of a toluene solution containing 2.04 g. (14.3 mmole) of diisobutylaluminium hydride, and the reaction mixture stirred for 30 minutes at the same temperature. Methanol was gradually added dropwise and, after the bubbling stopped, the resulting mixture was raised to 20°C., then stirred with 11 ml. of water for 30 minutes. The aluminum hydroxide which formed was filtered off and the residue was washed with an aqueous sodium chloride solution, dried over magnesium sulphate and concentrated at reduced pressure to obtain the title compound as a colourless oil: yield 1.72 g (97%).

TLC [ethyl acetate-cyclohexane mixture (1:1)] Rf = 0.51.

Following the same procedure but starting with a corresponding methyl α-dinor-16-methyl-prost-trans-13-enoate and methyl α-dinor-17-methyl-prost-trans-13-enoate, there were obtained 9α-hydroxy-11α,15α-bis(2-tetrahydropyranyloxy)-α-dinor-16-methyl-prost-trans-13-enaldehyde and 9α-hydroxy-11α,15α-bis(2-tetrahydropyranyloxy)-α-dinor-17-methyl-prost-trans-13-enaldehyde.

Similar products to those mentioned in this Reference Example can be obtained when the tetrahydropyranyl radical in the ester starting materials is replaced by the 1-ethoxyethyl group.

EXAMPLE 1

Synthesis of trans-$\Delta^2$-PGF$_{1\alpha}$

To a mixture of 472 mg. (purity: 63.9%; 12.5 mmole) of sodium hydride and 50 ml. of tetrahydrofuran was added dropwise 2.81 g. (12.5 mmole) of triethylphosphonoacetate, the reaction mixture being maintained at a temperature less than 30°C. Stirring was continued at 25°C., for 30 minutes until the generation of hydrogen stopped. 60 ml. of a tetrahydrofuran solution containing 1.72g.(3.58 mmole) of the title aldehyde product of Reference Example 4 was added thereto, and the resulting mixture was stirred for a further 40 minutes at 25°C., adjusted to pH 7 with acetic acid, diluted with water, extracted with diethyl ether and the ethereal extract washed with water, dried and concentrated. The residue was purified by silica gel column chromatography using an ethyl acetate-cyclohexane mixture (1:3) as eluent to obtain pure ethyl 9α-hydroxy-11α,15α-bis(2-tetrahydropyranyloxy)-prost-trans-2, trans-13-dienoate as a colourless oil; yield 1.53 g. (78%).

TLC [ethyl acetate-cyclohexane mixture (1:1)] Rf = 0.66

IR absorption spectrum (liquid film): 3440, 2930, 2840, 1720, 1650, 1130, 1020, and 970 cm$^{-1}$;

NMR spectrum (in CDCl$_3$): δ = 6.85 (1H, doublet-triplet), 5.69 (1H, doublet), 5.30 (2H, multiplet), 4.59 (2H, multiplet), 4.07 (2H, quartet), 4.1 – 3.2 (7H, multiplet).

A solution of 1.42 g. (2.59 mmole) of the ethyl ester compound in 15 ml. of tetrahydrofuran was mixed with 15 ml. of an aqueous solution containing 1.42 g. (25.9 mmole) of sodium hydroxide, and stirred for 2 hours at 25°C. The resulting mixture was diluted with 50 ml. of water, adjusted to pH 5 with oxalic acid, diluted further wiht 50 ml. of water, then extracted four times with 80 ml. of ethyl acetate. The ethyl acetate extract was washed with water, dried and concentrated under reduced pressure to obtain 1.42 g. of crude 9α-hydroxy-11α,15α-bis(2-tetrahydropyranyloxy)-prosta-trans-2,trans-13-dienoic acid.

The product thus obtained was dissolved in 125 ml. of a 1N hydrochloric acid-tetrahydrofuran mixture (1:1) and stirred for 1 hour at room temperature. After completion of the reaction, the reaction mixture was poured into 300 ml. of ice-water and extracted with ethyl acetate. The extract was washed with water, dried and concentrated under reduced pressure and the residue subjected to silica gel column chromatography using an ethyl acetate-cyclohexane mixture (5:1) as eluent to obtain pure trans-$\Delta^2$-PGF$_{1\alpha}$ as white crystals, m.p. 95°C; yield 580 mg. (59%).

IR absorption spectrum (potassium bromide tablet): 3320, 2900, 1700, 1640, 1420, 1310, 1020, and 960 cm$^{-1}$;

NMR spectrum (in acetone-d$_6$ solution): δ = 6.95 (1H, doublet-triplet), 5.81 (1H, doublet), 5.50 (2H, multiplet), 4.50 (4H, singlet), 4.00 (3H, multiplet).

EXAMPLE 2

Synthesis of trans-$\Delta^2$-PGE$_1$ 790 mg. of 9α-hydroxy-11α,15α-bis(2-tetrahydropyranloxy)-prosta-trans-2,trans-13-dienoic acid (prepared as described in Example 1) were dissolved in 24 ml. of diethyl water. The solution was cooled in an ice bath, and a solution prepared from 5 g. of manganese sulphate, 1.03 g. of chromium trioxide, 1.15 ml. of concentrated sulphuric acid and 23.9 ml. of water was added and the reaction mixture stirred for 2 hours at 0° to 5°C. 200 ml. of diethyl ether were added, and the resulting aqueous layer, after separation, was saturated with sodium sulphate and subjected to a further diethyl ether extraction.

The ethereal layers were combined, washed with water, dried and concentrated under reduced pressure. The residue was purified by silica gel column chromatography using a 6% ethanol-benzene mixture as eluent to obtain 710 mg. (88%) of 9-oxo-11α,15α-bis(2-tetrahydropyranyloxy)-prosta-trans-2,trans-13-dienoic acid as a colourless oil.

685 mg. (1.31 mmole) of the product thus obtained were dissolved in a mixed solvent containing 11.8 ml.

of acetic acid, 7.1 ml. of water and 1.42 ml. of tetrahydrofuran and the solution was stirred for 2 hours at 40°C. The reaction mixture was added to 60 ml. of ice-water, extracted with ethyl acetate, and the extract washed with water, dried and concentrated under reduced pressure. The residue was recrystallised from an ethyl acetate-cyclohexane mixture (1:1) to obtain the title compound as white needle-like crystals: yield 276 mg. (60%), m.p. 130° – 132°C.

IR absorption spectrum (potassium bromide tablet): 3480, 2900, 1736, 1705, 1655, 1283, 1195, 1080, and 975 cm$^{-1}$;

NMR spectrum (in CDCl$_3$ + methyl sulphoxide-d$_6$ solution): $\delta$ = 6.92 (1H, doublet-triplet), 5.77 (1H, doublet), 5.60 (2H, multiplet), 4.82 (3H, singlet), 4.00 (2H, multiplet), 2.72 (1H, doublet-doublet).

EXAMPLE 3

Synthesis of trans-$\Delta^2$-PGA$_1$

A solution of 170 mg. of trans-$\Delta^2$-PGE$_1$ (prepared as described in Example 2) in 15 ml. of 90% acetic acid was stirred for 17 hours at a temperature of 57° to 60°C. The reaction mixture was concentrated under reduced pressure and the residue dissolved in diethyl ether, washed with water, dried, and concentrated under reduced pressure. The residue was further purified by column chromatography using 20 g. of silica gel and a cyclohexane-ethyl acetate mixture (4:1) as eluent. The fraction containing trans-$\Delta^2$-PGA$_1$ was collected and concentrated. The product thus obtained was recrystallised from a cyclohexane-ethyl acetate mixture to obtain pure trans-$\Delta^2$-PGA$_1$: yield 102 mg. (63%), m.p. 68°C.

IR absorption spectrum (potassium bromide tablet): 2920, 1700, 1650, 1590, 1486, 1290, 975, 755 cm$^{-1}$;

NMR spectrum (in CDCl$_3$): $\delta$=7.50 (1H, doublet-doublet), 7.04 (doublet-doublet), 6.43 (2H singlet), 6.17 (1H, doublet-doublet), 5.82 (doublet), 5.62 (2H, multiplet), 4.11 (1H, multiplet) and 3.22 (1H, multiplet).

Following the same procedure but starting with 16-methyl-trans-$\Delta^2$-PGE$_1$ or 17-methyl-trans-$\Delta^2$-PGE$_1$ (prepared by an analogous procedure to that hitherto described for the preparation of trans-$\Delta^2$-PGE$_1$), there were obtained 16-methyl-trans-$\Delta^2$-PGA$_1$ and 17-methyl-trans-$\Delta^2$-PGA$_1$, the IR and NMR spectra of which were similar to those of trans-$\Delta^2$-PGA$_1$ except that in the NMR spectra the doublet peak of the methyl group appeared also at $\delta$=1.0 to 0.7.

REFERENCE EXAMPLE 5

Synthesis of 9$\alpha$-hydroxy-11$\alpha$,15$\alpha$-bis(2-tetrahydropyranyloxy)-$\alpha$-dinor-prostanoic acid A solution of 4.5 g. of 9$\alpha$-hydroxy-11$\alpha$,15$\alpha$-bis(2-tetrahydropyranyloxy)-$\alpha$-dinor-prosta-cis-and trans-5,trans-13-dienoic acids(prepared as described in Reference Example 2) in 60 ml. of ethanol was added to a suspension of 400 mg. of platinum oxide in 140 ml. of ethanol after being saturated with hydrogen. A hydrogen stream was passed through the stirred reaction mixture at 20°C., under ordinary pressure for 2 hours. The catalyst was removed by filtration and the filtrate was concentrated under reduced pressure to obtain 4.37 g. (97%) of the title compound.

Following the same procedure but starting with corresponding $\alpha$-dinor-prostadienoic acids with a methyl substituent on the carbon atom in the 16- or 17-position (prepared in an analogous manner to the preparation of 9$\alpha$-hydroxy-11$\alpha$,15$\alpha$-bis(2-tetrahydropyranyloxy)-$\alpha$-dinor-prosta-cis- and trans-5,trans-13-dienoic acids), there were obtained 9$\alpha$-hydroxy-11$\alpha$,15$\alpha$-bis(2-tetrahydropyranyloxy)-$\alpha$-dinor-16-methyl-prostanoic acid and 9$\alpha$-hydroxy-11$\alpha$,15$\alpha$-bis(2-tetrahydropyranyloxy)-$\alpha$-dinor-17-methyl-prostanoic acid.

Similar products to those mentioned in this Reference Example can be obtained from corresponding $\alpha$-dinor-prostadienoic acid starting materials in which the tetrahydropyranyl radical is replaced by the 1-ethoxyethyl group.

REFERENCE EXAMPLE 6

Synthesis of methyl 9$\alpha$-hydroxy-11$\alpha$,15$\alpha$-bis(2-tetrahydropyranyloxy)-$\alpha$-dinor-prostanoate A solution of 4.1 g. of the hydroxy acid title product of Reference Example 5 in 150 ml. of diethyl ether was mixed with a freshly prepared diethyl ether solution of diazomethane. The working up of the reaction mixture was conducted using the procedure described in Reference Example 3 to obtain 3.2 g. (76%) of the title compound.

IR absorption spectrum (liquid film): 3500, 2900, 1735, 1435, 1200, 1130, 1075, and 1020 cm$^{-1}$;

NMR spectrum (in CDCl$_3$): $\delta$ = 4.70 (2H, multiplet), 4.10 – 3.40 (7H, multiplet), 3.70 (3H, singlet); TLC [ethyl acetate-cyclohexane (1:1)] Rf = 0.64.

Following the same procedure but starting with corresponding $\alpha$-dinor-prostanoic acids with a methyl substituent on the carbon atom in the 16- or 17-position (prepared by the procedure of Reference Example 5), there were obtained methyl 9$\alpha$-hydroxy-11$\alpha$,15$\alpha$-bis(2-tetrahydropyranyloxy)-$\alpha$-dinor-16-methyl-prostanoate and methyl 9$\alpha$-hydroxy-11$\alpha$,15$\alpha$-bis(2-tetrahydropyranyloxy)-$\alpha$-dinor-17-methyl-prostanoate.

Similar products to those mentioned in this Reference Example can be obtained from corresponding $\alpha$-dinor-prostanoic acid starting materials in which the tetrahydropyranyl radical is replaced by the 1-ethoxyethyl group.

REFERENCE EXAMPLE 7

Synthesis of 9$\alpha$-hydroxy-11$\alpha$,15$\alpha$-bis(2-tetrahydropyranyloxy)-$\alpha$-dinor-prostanaldehyde 2.3 g. of the methyl ester title product of Reference Example 6 was reduced using the procedure described in Reference Example 4 to obtain 2.18 g. (95%) of the title aldehyde as a colourless oil.

TLC [ethyl acetate-cyclohexane (1:1)] Rf = 0.54.

In a similar manner but starting with methyl 9α-hydroxy-11α,15α-bis(2-tetrahydropyranyloxy)-α-dinor-16-methyl-prostanoate and methyl 9α-hydroxy-11α,15α-bis(2-tetrahydropyranyloxy)-α-dinor-17-methyl-prostanoate (cf. Reference Example 6), there were obtained 9α-hydroxy-11α,15α-bis(2-tetrahydropyranyloxy)-α-dinor-16-methyl-prostanaldehyde and 9α-hydroxy-11α,15α-bis(2-tetrahydropyranyloxy)-α-dinor-17-methyl-prostanaldehyde.

Similar products to those mentioned in this Reference Example can be obtained from corresponding methyl α-dinor-prostanoate starting materials in which the tetrahydropyranyl radical is replaced by the 1-ethoxyethyl group.

EXAMPLE 4

Synthesis of trans-Δ²-dihydro-PGE₁

1.8 g. of the aldehyde title product of Reference Example 7 was subjected to the Wittig reaction in accordance with the procedure described in Example 1 using sodium hydride and triethylphosphonoacetate to give the ethyl ester of 9α-hydroxy-11α,15α-bis(2-tetrahydropyranyloxy)-prost-trans-2-enoic acid as a colourless oil: yield 1.4 g. (67%).

IR absorption spectrum (liquid film): 3500, 2950, 1715, 1646, 1420, 1195, 1130, 1070, 1020, and 780 cm⁻¹;

NMR spectrum (in CDCl₃): δ = 6.80 (1H, doublet-triplet), 5.62 (1H, doublet), 4.49 (2H, multiplet), 4.02 (2H, quartet), 4.00 − 3.20 (7H, multiplet).

The ethyl ester thus obtained was hydrolysed with an alkaline solution in accordance with the procedure described in Example 1, the product oxidised with chromic acid according to the procedure described in Example 2, and the obtained PGE compound hydrolysed in an acidic solution. The resulting product, which was not crystallised, was subjected to silica gel column chromatography using a cyclohexane-ethyl acetate mixture (2:3) as eluent to obtain 562 mg. (63%) of the title compound as a colourless oil.

IR absorption spectrum (liquid film): 3360, 2900, 1730, 1690, 1650, 1455, 1240, 1120, 1045, 980, and 755 cm⁻¹;

NMR spectrum (in CDCl₃); δ = 7.02 (1H, doublet-triplet), 5.82 (1H, doublet), 5.65 (3H, singlet), 4.13 (1H, multiplet), 3.67 (1H, multiplet), 2.71 (1H, doublet-doublet).

In a similar manner but starting with 9α-hydroxy-11α,15α-bis(2-tetrahydropyranyloxy)-α-dinor-16-methyl-prostanaldehyde and 9α-hydroxy-11α,15α-bis(2-tetrahydropyranyloxy)-α-dinor-17-methyl-prostanaldehyde (cf. Reference Example 7), there were obtained 16-methyl-trans-Δ²-dihydro-PGE₁ and 17-methyl-trans-Δ²-dihydro-PGE₁.

Similar products to those mentioned in this Example can be obtained from corresponding α-dinor-prostanaldehyde starting materials in which the tetrahydropyranyl radical is replaced by the 1-ethoxyethyl group; the IR absorption and NMR spectra of the products were similar to those of trans-Δ²-dihydro-PGE₁ except that in the NMR spectrum the doublet peak of the methyl group appeared also at δ = 1.0 to 0.7.

REFERENCE EXAMPLE 8 synthesis of 9α-hydroxy-11α,15α-bis(2-tetrahydropyranyloxy)-16(R)-methyl-α-dinor-prost-trans-13-enoic acid A solution of 29 g. (0.070 mole) of 2-carboxyethyl-triphenylphosphonium bromide in 80 ml. of dimethylsulphoxide was mixed with a solution of sodiomethyl-sulphinylcarbanide [obtained from 5.0 g. (0.136 mole) of sodium hydride and dimethylsulphoxide] in 80 ml. of dimethylsulphoxide, the temperature of the reaction mixture being maintained at 25°C. To the resulting red mixture was added a solution of 10.5 g. (0.023 mole) of 2-oxa-3-hydroxy-6-syn-(3α-2'-tetrahydropyranyloxy-4(R)-methyl-oct-trans-1-enyl)-7-anti-(2-tetrahydropyranyloxy)-cis-bicyclo[3,3,0]-octane [prepared as described in French Pat. No. 7215314] in 80 ml. of dimethylsulphoxide. The reaction mixture was stirred for 2 hours at 25°C., poured into one liter of ice-water, 150 ml. of diethyl ether and 2 g. of potassium carbonate and then extracted with 150 ml. of ethyl acetate. The aqueous layer, after separation, was extracted three times with 250 ml. of diethyl ether-ethyl acetate (1:1) to remove the neutral substances, washed, acidified to pH 2 with oxalic acid and extracted 4 times with 500 ml. of diethyl ether-n-pentane (1:1). The organic layer, after separation, was washed with water, dried and concentrated under reduced pressure. The residue was purified using silica gel column chromatography and eluting with ethanolbenzene(6~10:100) to give 6.5 g. (55%) of 9α-hydroxy-11α,15α-bis(2-tetrahydropyranyloxy)-16(R)-methyl-α-dinor-prosta-cis-5,trans-13-dienoic acid as a colourless oil.

IR absorption spectrum (liquid film): 3420, 2930, 1710, 1440, 1375, 1245, 1135, 1023, 978 and 870 cm⁻¹;

NMR spectrum (in CDCl₃): δ = 7.20 (2H, singlet), 5.65 − 5.20 (4H, multiplet) and 4.67 (2H, multiplet).

The resulting compound was dissolved in 100 ml. of methanol mixed with 2.5 g. of 5% palladium on charcoal, and treated with hydrogen at room temperature until an equimolar amount of hydrogen had been absorbed. The catalyst was filtered off and the filtrate was concentrated under reduced pressure to yield 5.2 g. (79%) of the title compound.

TLC [dichloromethane-methanol (19:1)] Rf = 0.41.

REFERENCE EXAMPLE 9

Synthesis of methyl 9α-hydroxy-11α,15α-bis(2-tetrahydropyranyloxy)-16(R)-methyl-α-dinor-prost-trans-13-enoate 8.7 g. (0.017 mole) of 9α-hydroxy-11α,15α-bis(2-tetrahydropyranyloxy)-16(R)-methyl-α-dinor-prost-trans-13-enoic acid (prepared as described in Reference Example 8) were dissolved in 50 ml. of diethyl ether. A freshly prepared ethereal solution of diazomethane was added until the reaction mixture turned yellow. The mixture was then concentrated under reduced pressure at low temperature, and the residue was purified by column chromatography on silica gel using ethyl acetate-cyclohexane (1:1) as eluent.

IR absorption spectrum (liquid film): 3450, 2940, 1740, 1440, 1030 and 685 cm⁻¹;

NMR spectrum (in CDCl$_3$): δ = 5.63 – 5.30 (2H, multiplet), 4.70 (2H, multiplet), 3.64 (3H, singlet), and 4.20 –3.30 (7H, multiplet);

TLC [dichloromethane-methanol (19:1)] Rf. = 0.61.

REFERENCE EXAMPLE 10

Synthesis of 9α-hydroxy-11α,15α-bis(2-tetrahydropyranyloxy)-16(R)-methyl-α-dinor-prost-trans-13-enaldehyde 2.0 g. (0.0033 mole) of the methyl ester product of Reference Example 9 were dissolved in 54 ml. of toluene, and 8.2 ml. of a solution of 2.06 g. (0.0152 mole) of diisobutylaluminium hydride in toluene was added at −65°C. The reaction mixture was stirred at the same temperature for 30 minutes and methanol was added slowly dropwise until no more gas was evolved. The reaction mixture was allowed to warm to 20°C., 11 ml. of water was added and the mixture was stirred for 30 minutes. The solution was filtered to remove precipitated aluminium hydroxide, washed with brine, dried over magnesium sulphate and concentrated under reduced pressure to yield 1.83 g. (97.5%) of the title compound. TLC [cyclohexane — ethyl acetate (1:1)] Rf. = 0.52.

EXAMPLE 5

Synthesis of 16(R)-methyl-trans-Δ$^2$-PGF$_{1α}$

The procedure of Example 1 was repeated using as the starting material 9α-hydroxy-11α,15α-bis(2-tetrahydropyranyloxy)-α-dinor-16(R)-methyl-prost-trans-13-enaldehyde (prepared as described in Reference Example 10) to obtain ethyl 9α-hydroxy-11α,15α-bis(2-tetrahydropyranyloxy)-16(R)-methyl-prosta-trans-2,trans-13-dienoate as a colourless oil.

IR absorption spectrum (liquid film): 3400, 2950, 2860, 1725, 1650, 1135, 1020, and 970 cm$^{-1}$;

NMR spectrum (in CDCl$_3$): δ = 6.87 (1H, doublet-triplet), 5.67 (1H, doublet), 5.31 (2H, multiplet), 4.63 (2H, multiplet), 4.07 (quartet), 4.13 − 3.2 (7H, multiplet).

Following the same procedure but starting with corresponding α-dinor-prostenaldehydes with the methyl group on the carbon atom in the 16-position in the S- or the racemic configuration and/or with a methyl group on the carbon atom in the 17-position, there were obtained the corresponding ethyl prosta-trans-2, trans-13-dienoates, the IR spectra of which were similar to the 16(R)-methyl compound: the NMR spectra showed an additional peak (doublet) of the methyl group at δ = less than 1.0.

Using alkyl diethylphosphonoacetates, the esterifying alkyl group having 1 to 10 carbon atoms instead of triethylphosphonoacetate used in Example 1, there were obtained the corresponding alkyl esters of the prostadienoic acid, the IR spectra of which were very similar to those of the ethyl ester. The NMR spectra were similar to those of the ethyl ester except that the integral value of the methylene area changed and in that in the peaks depending upon the terminal esterifying alkyl group; there were, for example, methyl group at δ = 3.6, ethyl group at δ = 1.25, and groups higher than propyl group at still higher magnetic fields.

Using the procedure described in Example 1, the ethyl (or other alkyl) ester of 9α-hydroxy-11α,15α-bis(2-tetrahydropyranyloxy)-16(R)-methyl-prosta-trans-2, trans-13-dienoic acid obtained as described above was successively hydrolysed in alkaline solution to give 9α-hydroxy-11α,15α-bis(2-tetrahydropyranyloxy)-16(R)-methyl-prosta-trans-2, trans-13-dienoic acid, then in acidic solution and finally purified to obtain pure 16(R)-methyl-trans-Δ$^2$-PGF$_{1α}$ as a colourless oil.

IR absorption spectrum (liquid film): 3330, 2950 − 2860, 2400, 1700, 1640, 1420, 1305, 1025 and 970 cm$^{-1}$;

NMR spectrum (in acetone-d$_6$ solution): δ = 6.92 (1H, doublet-triplet), 5.81 (1H, doublet), 5.52 (2H, multiplet), 4.78 (4H, singlet), 4.02 (3H, multiplet), 1.05 − 0.86 (6H, doublet and triplet);

optical rotation [α]$_D^{25}$ = +32.0° (c = 0.60, ethanol).

Following the same procedure but starting with the ethyl 9α-hydroxy-11α,15α-bis(2-tetrahydropyranyloxy)-16(S)[or 16($\frac{R}{S}$)]-methyl-prosta-trans-2, trans-13-dienoate or ethyl 9α-hydroxy-11α,15α-bis(2-tetrahydropyranyloxy)-17-methyl-prosta-trans-2, trans-13-dienoate, there were obtained, via the corresponding dienoic acids, 16(S)-methyl-trans-Δ$^2$-PGF$_{1α}$, 16($\frac{R}{S}$)-methyl-trans-Δ$^2$-PGF$_{1α}$ and 17-methyl-trans-Δ$^2$-PGF$_{1α}$, the IR and NMR spectra of which were similar to those of trans-Δ$^2$-PGF$_{1α}$ except that the doublet peak of the methyl group appeared also at δ = 1.0 to 0.7.

EXAMPLE 6

Synthesis of 16(R)-methyl-trans-Δ$^2$-PGE$_1$ 1.03 g. (1.92 mmole) of 9α-hydroxy-11α,15α-bis(2-tetrahydropyranyloxy)-16(R)-methyl-prosta-trans-2, trans-13-dienoic acid (prepared as described in Example 5) was dissolved in 40 ml. of diethyl ether, cooled in an icebath, and a solution of 5.2 g. of manganese sulphate, 1.1 g. of chromium trioxide, 1.40 ml. of sulphuric acid and 24 ml. of water, was added and the reaction mixture stirred at 0° to 5°C. for 2 hours. Diethyl ether was added to the reaction mixture and the ethereal layer separated. The aqueous layer was saturated with sodium sulphate and extracted with diethyl ether. The combined ethereal extracts were washed with water, dried over magnesium sulphate and concentrated under reduced pressure. The residue was purified by silica gel column chromatography using ethanol — benzene (6:94) as eluent to give 815 mg. (80%) of 9-oxo-11α,15α-bis(2-tetrahydropyranyloxy)-16(R)-methyl-prosta-trans-2,trans-13-dienoic acid.

815 mg. (1.55 mmole) of the compound thus obtained was dissolved in a mixed solvent of 20 ml. of acetic acid — water — tetrahydrofuran (65:35:10) and the solution stirred at 40°C., for 2 hours. 70 ml. of ice-water were added to the solution which was then extracted with ethyl acetate. The combined extracts were washed with water, dried and concentrated under reduced pressure. The residue was purified by silica gel column chromatography using cyclohexane — ethyl acetate (1:1) as eluent to obtain 347 mg. (62%) of the title compound IR absorption spectrum (liquid film): 3370, 2920, 1735, 1700, 1645, 1450, 1380, 1245, 1080, 980 cm$^{-1}$;

NMR spectrum (in CDCl$_3$): δ = 6.99 (1H, doublet-triplet), 5.80 (1H, doublet), 5.70 − 5.30 (5H, multiplet), 4.20 − 3.80 (2H, multiplet), 2.74 (1H, doublet-doublet);

TLC [chloroform — tetrahydrofuran — acetic acid (10:2:1)] Rf. = 0.27;

Optical Rotation $[\alpha]_D^{25} = -48.0°$ (c = 0.95, ethanol).

EXAMPLE 7

Synthesis of 16(R)-methyl-trans-$\Delta^2$-PGA$_1$ 192 mg. (0.524 mmole) of 16(R)-methyl-trans-$\Delta^2$-PGE$_1$ (prepared as described in Example 6) were dissolved in 15 ml. of 90% acetic acid and the solution was stirred at 57° – 60°C. for 17 hours. The reaction mixture was concentrated under reduced pressure, the residue dissolved in diethyl ether, the ethereal solution washed with water, dried and concentrated under reduced pressure. The residue was purified by column chromatography on silica gel using cyclohexane — ethyl acetate (4:1) as eluent to yield 122 mg. (67%) of the title compound.

IR absorption spectrum (liquid film): 3400, 2700 – 2300, 1710, 1660, 1595, 1460, 980 cm$^{-1}$;

NMR spectrum (in CDCl$_3$): $\delta$ = 7.48 (1H, doublet-doublet), 7.03 (1H, doublet-triplet), 6.17 (1H, doublet-doublet), 5.95 – 5.45 (5H, multiplet), 3.99 (1H, multiplet); TLC [chloroform — tetrahydrofuran — acetic acid (10:2:1)] Rf. = 0.69;

Optical Rotation: $[\alpha]_D^{25} = +171.1°$ (c = 0.80 ethanol);
Ultra-violet (UV) absorption spectrum: $\lambda_{max}$ = 213 m$\mu$ (in 50% ethanol).

EXAMPLE 8

Synthesis of 17-methyl-trans-$\Delta^2$-PGE$_1$

The procedure described in Example 2 was repeated using 9$\alpha$-hydroxy-11$\alpha$,15$\alpha$-bis(2-tetrahydropyranyloxy)-17-methyl-prosta-trans-2,trans-13-dienoic acid (prepared as described in Example 5) instead of 9$\alpha$-hydroxy-11$\alpha$,15$\alpha$-bis(2-tetrahydropyranyloxy)-prosta-trans-2,trans-13-dienoic acid to give 17-methyl-trans-$\Delta^2$-PGE$_1$ as a colourless oil.

IR absorption spectrum (liquid film): 3400, 2960 – 2860, 1740, 1710, 1650, 1460, 1280, 1200, 1080 and 980 cm$^{-1}$;

NMR spectrum (in CDCl$_3$): $\delta$ = 6.89 (1H, doublet-triplet), 5.80 (1H, doublet), 5.56 (2H, multiplet), 4.90 (3H, singlet), 4.05 (2H, multiplet), 2.74 (1H, doublet-doublet), 1.00 – 0.74 (6H, triplet and doublet).

The same procedure was repeated using a compound having a methyl group in the 16-position prepared in Example 5 as the starting compound to obtain the corresponding 16-methyl-trans-$\Delta^2$-PGE$_1$ therefrom; the IR and NMR spectra of the product were similar to those of trans-$\Delta^2$-PGE$_1$ except that the doublet peak of the methyl group appeared also at $\delta$ = 1.0 to 0.7.

REFERENCE EXAMPLE 11

Synthesis of 2-oxa-3-hydroxy-6-syn-(3$\alpha$-2'-tetrahydropyranyloxy-4-cyclopentyl-pent-trans-1-enyl)-7-anti-(2-tetrahydropyranyloxy)-cis-bicyclo-[3,3,0]octane A methanolic solution of 6.5 g. of 2-oxa-3-oxo-6-syn-(3$\alpha$-hydroxy-4-cyclopentyl-pent-trans-1-enyl)-7-anti-acetoxy-cis-bicyclo[3,3,0]octane [obtained by appropriate modification of the procedure described in J. Amer. Chem. Soc. 92, 397 (1970)] was hydrolysed with an equimolar aqueous potassium carbonate solution at 25°C., to obtain 5.5 g. (100%) of 2-oxa-3-oxo-6-syn-(3$\alpha$-hydroxy-4-cyclopentyl-pent-trans-1-enyl)-7-anti-hydroxy-cis-bicyclo[3,3,0]octane.

A methylene chloride solution of 5.6 g. of the hydroxy compound thus obtained was reacted with 10 equimolar amounts of dihydropyran and a small amount of p-toluenesulphonic acid as catalyst at 25°C., for 15 minutes to yield 8.9 g. (100%) of 2-oxa-3-oxo-6-syn-(3$\alpha$-2'-tetrahydropyranyloxy-4-cyclopentyl-pent-trans-1-enyl)-7-anti-(2-tetrahydropyranyloxy)-cis-bicyclo[3,3,0]octane.

8.6 g. of the said bis-tetrahydropyranyl compound in toluene was reduced with 2 equimolar amounts of diisobutylaluminium hydride at −60°C. for 30 minutes to yield 8.6 g. (100%) of the title compound.

REFERENCE EXAMPLE 12

Synthesis of 9$\alpha$-hydroxy-11$\alpha$,15$\alpha$-bis(2-tetrahydropyranyloxy)-16-phenyl-$\alpha$-dinor-$\omega$-trinor-prost-trans-13-enoic acid A solution of 88 g. (0.212 mole) of 2-carboxyethyl-triphenylphosphonium bromide in 170 ml. of dimethylsulphoxide was mixed with 202 ml. of dimethylsulphoxide containing 2 molecular equivalents of sodiomethylsulphinyl carbanide (0.404 mole as sodiomethylsulphinyl carbanide) whilst maintaining the temperature at 25°C. To the resulting red mixture was added a solution containing 33.4 g. (0.0706 mole) of 2-oxa-3-hydroxy-6-syn-(3$\alpha$-2' tetrahydropyranyloxy-4-phenyl-pent-trans-1-enyl)-7-anti-(2-tetrahydropyranyloxy)-cis-bicyclo[3,3,0]octane (prepared by a similar procedure to that described in Reference Example 11) in 150 ml. of dimethylsulphoxide. The reaction mixture was stirred for 2 hours at 25°C., poured into 3 liters of ice-water, 350 ml. of diethyl ether and 5g. of potassium carbonate and then extracted with 350 ml. of ethyl acetate. The aqueous layer was extracted three times with 700 ml. of a diethyl ether-ethyl acetate mixture (1:1), washed to remove the neutral substances, adjusted to pH 2 with oxalic acid and extracted four times with 1.4 liters of a diethyl ether-pentane mixture (1:1); the organic layer was washed with water, dried and concentrated under reduced pressure. The residue was purified by silica gel column chromatography using an ethanol-benzene mixture (6~10:100) as eluent to give 18.1 g. (48%) of 9$\alpha$-hydroxy-11$\alpha$, 15$\alpha$-bis(2-tetrahydropyranyloxy)-16-phenyl-$\alpha$-dinor-$\omega$-trinor-prosta-cis-5, trans-13-dienoic acid as a colourless oil.

IR absorption spectrum (liquid film): 3450, 3030, 2940, 1705, 1450, 1244, 1023, 977 and 689 cm$^{-1}$.

NMR spectrum (in CDCl$_3$): $\delta$ = 7.12 (5H, multiplet), 6.53 (2H, singlet), 5.60 – 5.20 (4H, multiplet), 4.65 (2H, multiplet).

The compound thus obtained was dissolved in 185 ml. of methanol, mixed with 8.5 g. of 5% palladium on charcoal and treated with hydrogen; after absorption of an equimolar amount of hydrogen at room temperature, the catalyst was filtered off and the filtrate was concentrated under reduced pressure to yield 15.1 g. (83%) of the title compound. TLC [methylene chloride-methanol (19:1)] Rf. = 0.40.

REFERENCE EXAMPLE 13

Using the procedure described in Reference Example 12, the following compounds were obtained:

a. 9$\alpha$-hydroxy-11$\alpha$, 15$\alpha$-bis(2-tetrahydropyranyloxy)-16-cyclohexyl-$\alpha$-dinor-$\omega$-trinor-prost-trans-13-enoic acid 88 g. (0.212 mole) of 2-carboxyethyl-triphenylphosphonium bromide and 33.8 g. of 2-oxa-3-hydroxy-6-syn-(3$\alpha$-2'-tetrahydropyranyloxy-4-cyclohexyl-pent-trans-1-enyl)-7-anti-(2-tetrahydropyranyloxy)-cis-bicyclo[3,3,0]-octane (prepared by a similar procedure to that described in Reference Example 11) gave 15.7 g. (41%) of the title compound.

TLC [methylene chloride-methanol (19:1)] Rf. = 0.32.

b. 9α-hydroxy-11α, 15α-bis(2-tetrahydropyranyloxy)-16-cyclopentyl-α-dinor-ω-trinor-prost-trans-13-enoic acid 88 g. (0.212 mole) of 2-carboxyethyl-triphenylphosphonium bromide and 33.0 g. of 2-oxa-3-hydroxy-6-syn-(3α-2'-tetrahydropyranyloxy-4-cyclopentyl-pent-trans-1-enyl)-7-anti-(2-tetrahydropyranyloxy)-cis-bicyclo[3,3,0]octane (prepared as described in Reference Example 11) gave 15.2 g. (40.5%) of the title compound.

TLC [methylene chloride-methanol (19:1)] Rf. = 0.30.

c. 9α-hydroxy-11α, 15-bis(2-tetrahydropyranyloxy)-15-methyl-α-dinor-prost-trans-13-enoic acid 88 g. (0.212 mole) of 2-carboxyethyl-triphenylphosphonium bromide and 33.0 g. of 2-oxa-3-hydroxy-6-syn-(3-2'-tetrahydropyranyloxy-3-methyl-oct-trans-1-enyl)-7-anti-(2-tetrahydropyranyloxy)-cis-bicyclo-[3,3,0]octane (prepared by a similar procedure to that described in Reference Example 11) gave 15.5 g. (41.0%) of the title compound.

TLC [methylene chloride-methanol (19:1)] R.f. = 0.41.

d. 9α-hydroxy-11α, 15-bis(2-tetrahydropyranyloxy)-15,16-dimethyl-α-dinor-prost-trans-13-enoic acid 88 g. (0.212 mole) of 2-carboxyethyl-triphenylphosphonium bromide and 34.0 g. of 2-oxa-3-hydroxy-6-syn-(3-2'-tetrahydropyranyloxy-3,4-dimethyl-oct-trans-1-enyl)-7-anti-(2-tetrahydropyranyloxy)-cis-bicyclo-[3,3,0]octane (prepared by a similar procedure to that described in Reference Example 11) gave 15.8 g. (40.9%) of the title compound.

TLC [methylene chloride-methanol (19:1)] Rf. = 0.42.

REFERENCE EXAMPLE 14

Synthesis of methyl 9α-hydroxy-11α, 15α-bis(2-tetrahydropyranyloxy)-16-phenyl-α-dinor-ω-trinor-prost-trans-13-enoate 3.16 g. (5.94 mmole) of 9α-hydroxy-11α, 15α-bis(2-tetrahydropyranyloxy)-16-phenyl-α-dinor-ω-trinor-prost-trans-13-enoic acid (obtained as described in Reference Example 12) were dissolved in 100 ml. of diethyl ether. A freshly prepared ethereal solution of diazomethane was added until the reaction mixture turned yellow. The mixture was then concentrated under reduced pressure at low temperature, and the residue was purified by column chromatography on silica gel using ethyl acetate-cyclohexane (1:1) as eluent to yield 2.61 g. (80%) of the title compound.

IR absorption spectrum (liquid film): 3430, 3030, 2940, 1735, 1450, 1023 and 690 cm$^{-1}$;

NMR spectrum (in CDCl$_3$): δ = 7.12 (5H, multiplet), 5.50 − 5.15 (2H, multiplet), 4.55 (2H, multiplet), 3.57 (3H, singlet), 4.10 − 3.20 (7H, multiplet);

TLC [methylene chloride-methanol (19:1)] Rf. = 0.60.

REFERENCE EXAMPLE 15

Using the procedure described in Reference Example 14, the following compounds were obtained:

a. Methyl 9α-hydroxy-11α, 15α-bis(2-tetrahydropyranyloxy)-16-cyclohexyl-α-dinor-ω-trinor-prost-trans-13-enoate From 3.2 g. (5.9 mmole) of 9α-hydroxy-11α, 15α-bis(2-tetrahydropyranyloxy)-16-cyclohexyl-α-dinor-ω-trinor-prost-trans-13-enoic acid (prepared as described in Reference Example 13 (a)), there were obtained 2.63 g. (80%) of the title compound.

IR absorption spectrum (liquid film): 3420, 2900, 2820, 1735, 1440, 1200, 1120, 1020 and 902 cm$^{-1}$;

NMR spectrum (in CDCl$_3$): δ = 5.50 − 5.20 (2H, multiplet), 4.60 (2H, multiplet), 3.52 (3H, singlet), 4.10 − 3.20 (7H, multiplet);

TLC [methylene chloride-methanol (19:1)] Rf. = 0.55.

b. Methyl 9α-hydroxy-11α,15α-bis(2-tetrahydropyranyloxy)-16-cyclopentyl-α-dinor-ω-trinor-prost-trans-13-enoate From 3.15 g. (5.95 mmole) of 9α-hydroxy-11α,15α-bis(2-tetrahydropyranyloxy)-16-cyclopentyl-α-dinor-ω-trinor-prost-trans-13-enoic acid (prepared as described in Reference Example 13(b)), 2.6 g. (80.5%) of the title compound were obtained.

IR absorption spectrum (liquid film): 3450, 2920, 2820, 1735, 1440, 1200, 1120, 1020 and 970 cm$^{-1}$;

NMR spectrum (in CDCL$_3$): δ = 5.50 − 5.23 (2H, multiplet), 4.60 (2H, multiplet), 3.60 (3H, singlet), 4.10 − 3.20 (7H, multiplet), 0.87 (3H, doublet);

TLC [methylene chloride-methanol (19:1)] Rf. = 0.75.

c. Methyl 9α-hydroxy-11α,15-bis(2-tetrahydropyranyloxy)-15-methyl-α-dinor-prost-trans-13-enoate From 3.04 g. (5.9 mmole) of 9α-hydroxy-11α,15-bis(2-tetrahydropyranloxy)-15-methyl-α-dinor-prost-trans-13-enoic acid (prepared as described in Reference Example 13(c)), 2.5 g. (80%) of the title compound were obtained. IR absorption spectrum (liquid film): 3440, 2920, 2850, 1935, 1200, 1120, 1020 and 975 cm$^{-1}$;

NMR spectrum (in CDCl$_3$): δ = 5.60 − 5.25 (2H, multiplet), 4.65 (2H, multiplet), 3.57 (3H, singlet), 4.10 − 3.30 (6H, multiplet);

TLC [methylene chloride-methanol (19:1)] Rf. = 0.61.

d. Methyl 9α-hydroxy-11α,15-bis(2-tetrahydropyranyloxy)-15,16-dimethyl-α-dinor-prost-trans-13-enoate From 3.15 g. (5.95 mmole) of 9α-hydroxy-11α,15-bis(2-tetrahydropyranyloxy)-15,16-dimethyl-α-dinor-prost-trans-13-enoic acid (prepared as described in Reference Example 13(d)), 2.6 g. (80.5%) of the title compound were obtained.

IR absorption spectrum (liquid film): 3440, 2920, 2845, 1736, 1200, 1120, 1020 and 980 cm$^{-1}$;

NMR spectrum (in CDCl$_3$): δ = 5.65 − 5.30 (2H, multiplet), 4.64 (2H, multiplet), 4.10 − 3.30 (6H, multiplet, 3.59 (3H, singlet);

TLC [methylene chloride-methanol (19:1)] Rf. = 0.62.

REFERENCE EXAMPLE 16

Synthesis of 9α-hydroxy-11α,15α-bis(2-tetrahydropyranyloxy)-16-phenyl-α-dinor-ω-trinor-prost-trans-13-enaldehyde 1.96 g. (3.58 mmole) of the methyl ester product of Reference Example 14 were dissolved in 54 ml. of toluene, and 8.14 ml. of a solution of 2.04 g. (14.3 mmole) of diisobutylaluminiumhydride in toluene were added at −65°C. The solution was stirred at the same temperature for 30 minutes and methanol was slowly added dropwise until no more gas was evolved. The reaction mixture was allowed to warm to 20°C., 11 ml. of water were added and the mixture was stirred for 30 minutes. The solution was filtered to remove precipitated aluminium hydroxide, washed with brine, dried over magnesium sulphate, and concentrated under reduced pressure to yield 1.79 g. (97%) of the title compound.

TLC [cyclohexane-ethyl acetate (1:1)] Rf. = 0.53.

REFERENCE EXAMPLE 17

Using the same procedure as in Reference Example 16, the following compounds were obtained:

a. 9α-hydroxy-11α,15α-bis(2-tetrahydropyranyloxy)-16-cyclohexyl-α-dinor-ω-trinor-prost-trans-13-enaldehyde 1.99 g. (3.6 mmole) of the methyl ester compound prepared in Reference Example 15(a) gave 1.84 g. (97.5%) of the title compound.

TLC [methylene chloride-methanol (19:1)] Rf. = 0.51.

b. 9α-hydroxy-11α,15α-bis(2-tetrahydropyranyloxy)-16-cyclopentyl-α-dinor-ω-trinor-prost-trans-13-enaldehyde 1.94 g. (3.6 mmole) of the methyl ester compound prepared in Reference Example 15(b) gave 1.78 g. (97%) of the title compound.

TLC [cyclohexane-ethyl acetate (1:1)] Rf. = 0.55.

c. 9α-hydroxy-11α,15-bis(2-tetrahydropyranyloxy)-15-methyl-α-dinor-prost-trans-13-enaldehyde 1.90 g. (3.6 mmole) of the methyl ester compound prepared in Reference Example 15(c) gave 1.74 g. (97.1%) of the title compound.

TLC [cyclohexane-ethyl acetate (1:1)] Rf. = 0.54.

d. 9α-hydroxy-11α,15-bis(2-tetrahydropyranyloxy)-15,16-dimethyl-α-dinor-prost-trans-13-enaldehyde 1.94 g. (3.6 mmole) of the methyl ester compound prepared in Reference Example 15(d) gave 1.78 g. (97%) of the title compound.

TLC [cyclohexane-ethyl acetate (1:1)] Rf. = 0.55.

EXAMPLE 9

Synthesis of ethyl 9α-hydroxy-11α,15α-bis(2-tetrahydropyranyloxy)-16-phenyl-ω-trinor-prosta-trans-2,trans-13-dienoate To a mixture of 472 mg. (purity 63.9%; 12.5 mmole) of sodium hydride and 50 ml. of tetrahydrofuran, 2.81 g. (12.5 mmole) of triethylphosphonacetate was added dropwise, keeping the temperature below 30°C. The mixture was stirred at 25°C., for about 30 minutes until evolution of hydrogen ceased.

A solution of 1.85 g. (3.58 mmole) of the aldehyde prepared in Reference Example 16 in 60 ml. of tetrahydrofuran was added to the reaction mixture which was then stirred at 25°C., for 40 minutes. The pH of the solution was adjusted to pH 7 with acetic acid, the solution was diluted with water and extracted with diethyl ether. The ethereal layer was washed with water, dried and concentrated.

The residue was purified by silica gel column chromatography using ethyl acetate-cyclohexane (1:3) as eluent to yield 1.62 g. (77%) of the title compound.

IR absorption spectrum (liquid film): 3450, 3030, 2940, 1720, 1650, 1023 and 690 cm$^{-1}$;

NMR spectrum (in CDCl$_3$): ω = 7.12 (5H, multiplet), 6.85 (1H, double-triplet), 5.68 (1H, doublet), 5.50 − 5.20 (2H, multiplet), 4.60 (2H, multiplet), 4.09 (2H, quartet), 4.10 − 3.20 (7H, multiplet);

TLC [cyclohexane-ethyl acetate (1:1)] Rf. = 0.68.

EXAMPLE 10

Synthesis of ethyl 9α-hydroxy-11α,15α-bis(2-tetrahydropyranyloxy)-16-cyclohexyl-ω-trinor-prosta-trans-2,trans-13-dienoate Using the procedure described in Example 9, 1.87 g. (3.6 mmole) of the aldehyde prepared as described in Reference Example 17(a) gave 1.64 g. (77.3%) of the title compound.

IR absorption spectrum (liquid film): 3450, 2900, 2820, 1720, 1650, 1120, 1020 and 902 cm$^{-1}$;

NMR spectrum (in CDCl$_3$): δ = 6.84 (1H, doublet-triplet), 5.66 (1H, doublet), 5.50 − 5.20 (2H, multiplet), 4.60 (2H, multiplet), 4.08 (2H, quartet), 4.10 − 3.20 (7H, multiplet);

TLC [cyclohexane-ethyl acetate (1:1)] Rf. = 0.66.

EXAMPLE 11

Synthesis of ethyl 9α-hydroxy-11α,15α-bis(2-tetrahydropyranyloxy)-16-cyclopentyl-ω-trinor-prosta-trans-2,-trans-13-dienoate The procedure described in Example 9 was followed using 1.82 g. (3.6 mmole) of the aldehyde prepared as described in Reference Example 17(b) as starting material to yield 1.60 g. (77.1%) of the title compound.

IR absorption spectrum (liquid film): 3450, 2920, 2830, 1720, 1650, 1120, 1020 and 978 cm$^{-1}$;

NMR spectrum (in CDCl$_3$): δ = 6.85 (1H, doublet-triplet), 5.65 (1H, doublet), 5.50 − 5.20 (2H, multiplet), 4.62 (2H, multiplet), 4.07 (2H, quartet), 4.10 − 3.20 (7H, multiplet), 0.88 (3H, doublet);

TLC [cyclohexane-ethyl acetate (1:1)] Rf. = 0.67.

EXAMPLE 12

Synthesis of ethyl 9α-hydroxy-11α,15-bis(2-tetrahydropyranyloxy)-15-methyl-prosta-trans-2,trans-13-dienoate Using the procedure described in Example 9 1.77 g. (3.6 mmole) of the aldehyde prepared as described in Reference Example 17(c) gave 1.56 g. (77%) of the title compound.

IR absorption spectrum (liquid film): 3450, 2920, 2840, 1720, 1650, 1130, 1020 and 975 cm$^{-1}$;

NMR spectrum (in CDCl$_3$): δ = 6.86 (1H, doublet-triplet), 5.68 (1H, doublet), 5.60 − 5.25 (2H, multiplet), 4.62 (2H, multiplet), 4.10 (2H, quartet), 4.10−3.35 (6H, multiplet);

TLC [cyclohexane-ethyl acetate (1:1)] Rf. = 0.69.

EXAMPLE 13

Synthesis of ethyl 9α-hydroxy-11α,15-bis(2-tetrahydropyranyloxy)-15,16-dimethyl-prosta-trans-2,trans-13-dienoate The procedure described in Example 9 was followed using 1.82 g. (3.6 mmole) of the aldehyde prepared as described in Reference Example 17(d) as a starting material to yield 1.62 g. (78%) of the title compound.

IR absorption spectrum (liquid film): 3450, 2920, 2840, 1720, 1652, 1120, 1020 and 980 cm$^{-1}$;

NMR spectrum (in $CDCl_3$): δ = 6.86 (1H, doublet-triplet), 5.68 (1H, doublet), 5.70 − 5.30 (2H, multiplet), 4.65 (2H, multiplet), 4.10 (2H, quartet), 4.10 − 3.30 (6H, multiplet);

TLC [cyclohexane-ethyl acetate (1:1)] Rf. = 0.70.

EXAMPLE 14

Synthesis of 9α-hydroxy-11α,15α-bis(2-tetrahydropyranyloxy)-16-phenyl-ω-trinor-prosta-trans-2,trans-13-dienoic acid 1.51 g. (2.59 mmole) of the ethyl ester prepared as described in Example 9 was dissolved in 15 ml. of tetrahydrofuran. After addition of 15 ml. of an aqueous solution containing 1.42 g. (25.9 mmole) of potassium hydroxide, the solution was stirred at 25°C., for 2 hours. 50 ml. of water was added to the reaction mixture and the solution adjusted to pH 5 with oxalic acid; a further 50 ml. of water was added and the solution extracted four times with 80 ml. of ethyl acetate. The organic layer was washed with water, dried and concentrated under reduced pressure. The residue was purified by silica gel column chromatography using benzene-ethyl acetate (3:1) as eluent to yield 1.11 g. (77%) of the title compound.

IR absorption spectrum (liquid film): 3400, 3030, 2940, 1700, 1640, 1023 and 690 $cm^{-1}$;

NMR spectrum (in $CDCl_3$): δ = 7.12 (5H, multiplet), 6.95 (1H, doublet-triplet), 6.40 (2H, singlet), 5.80 (1H, doublet), 5.50 − 5.20 (2H, multiplet), 4.60 (2H, multiplet), 4.10 − 3.20 (7H, multiplet);

TLC [methylene chloride-methanol (19:1)] Rf. = 0.28.

EXAMPLE 15

Using the procedure described in Example 14, the following compounds were obtained:
 a. 9α-hydroxy-11α,15α-bis(2-tetrahydropyranyloxy)-16-cyclohexyl-ω-trinor-prosta-trans-2,trans-13-dienoic acid 1.53 g. (2.6 mmole) of the ethyl ester prepared as described in Example 10 gave 1.13 g. (77.3%) of the title compound.

IR absorption spectrum (liquid film): 3400, 2900, 2820, 1700, 1642, 1120, 1020 and 902 $cm^{-1}$;

NMR spectrum (in $CDCl_3$): δ = 6.92 (1H, doublet-triplet), 6.30 (2H, singlet), 5.77 (1H, doublet), 5.50 − 5.20 (2H, multiplet), 4.55 (2H, multiplet), 4.10 − 3.20 (7H, multiplet);

TLC [methylene chloride-methanol (19:1)] Rf. = 0.26.
 b. 9α-hydroxy-11α,15α-bis(2-tetrahydropyranyloxy)-16-cyclopentyl-ω-trinor-prosta-trans-2,trans-13-dienoic acid 1.50 g. (2.6 mmole) of the ethyl ester prepared as described in Example 11 gave 1.09 g. (76.5%) of the title compound.

IR absorption spectrum (liquid film): 3400, 2920, 2830, 1700, 1642, 1120, 1020 and 977 $cm^{-1}$;

NMR spectrum (in $CDCl_3$): δ = 6.90 (1H, doublet-triplet), 6.00 (2H, singlet), 5.76 (1H, doublet), 5.50 − 5.20 (2H, multiplet), 4.60 (2H, multiplet), 4.10 − 3.20 (7H, multiplet), 0.87 (3H, doublet);

TLC [methylene chloride-methanol (19:1)] Rf. = 0.27.
 c. 9α-hydroxy-11α,15-bis(2-tetrahydropyranyloxy)-15-methyl-prosta-trans-2,trans-13-dienoic acid 1.46 g. (2.6 mmole) of the ethyl ester prepared as described in Example 12 gave 1.07 g. (77.1%) of the title compound.

IR absorption spectrum (liquid film): 3400, 2920, 2820, 1698, 1642, 1130, 1020 and 975 $cm^{-1}$;

NMR spectrum (in $CDCl_3$): δ = 6.92 (1H, doublet-triplet), 6.13 (2H, singlet), 5.77 (1H, doublet), 5.60 − 5.20 (2H, multiplet), 4.60 (2H, multiplet), 4.10−3.30 (6H, multiplet);

TLC [methylene chloride-methanol (19:1)] Rf. = 0.29.
 d. 9α-hydroxy-11α,15-bis(2-tetrahydropyranyloxy)-15,16-dimethyl-prosta-trans-2,trans-13-dienoic acid 1.50 g. (2.6 mmole) of the ethyl ester prepared as described in Example 13 gave 1.08 g. (75.7%) of the title compound:

IR absorption spectrum (liquid film): 3400, 2920, 2840, 1700, 1640, 1130, 1020 and 980 $cm^{-1}$;

NMR spectrum (in $CDCl_3$): δ = 6.92 (1H, doublet-triplet), 6.00 (2H, singlet), 5.76 (1H, doublet), 5.70 − 5.30 (2H, multiplet), 4.63 (2H, multiplet), 4.10 − 3.30 (6H, multiplet);

TLC [methylene chloride-methanol (19:1)] Rf. = 0.30

EXAMPLE 16

Synthesis of 16-phenyl-ω-trinor-trans-$\Delta^2$-$PGF_{1\alpha}$ 1.06 g. (1.9 mmole) of the carboxylic acid prepared as described in Example 14 was dissolved in 125 ml. of a mixture of N hydrochloric acid-tetrahydrofuran (1:1), and the solution stirred at room temperature for 1 hour. The reaction mixture was poured into 300 ml. of ice-water, extracted with ethyl acetate, and the organic layer was washed with water, dried and concentrated under reduced pressure. The residue was purified by silica gel column chromatography using ethyl acetate-cyclohexane (5:1) as eluent to yield 575 mg. (78%) of the title compound.

IR absorption spectrum (liquid film): 3330, 1698, 1640, 980 and 680 $cm^{-1}$;

NMR spectrum (in $CDCl_3$): δ = 7.25 (5H, multiplet), 6.96 (1H, doublet-triplet), 5.81 (1H, doublet), 5.50 (2H, multiplet), 5.00 (4H, singlet), 4.20 − 3.80 (3H, multiplet), 2.75 (1H, multiplet), 1.21 (3H, doublet);

TLC [chloroform-tetrahydrofuran-acetic acid (10:2:1)] Rf. = 0.20.

EXAMPLE 17

Using the procedure described in Example 16, the following compounds were obtained:
 a. 16-cyclohexyl-ω-trinor-trans-$\Delta^2$-$PGF_{1\alpha}$ 1.11 g. (1.9 mmole) of the carboxylic acid prepared as described in Example 15(a) gave 575 mg. (76.8%) of the title compound.

IR absorption spectrum (liquid film): 3330, 1700, 1642, 960 and 902 $cm^{-1}$;

NMR spectrum (in $CDCl_3$): δ = 6.95 (1H, doublet-triplet), 5.80 (1H, doublet), 5.41 (2H, multiplet), 4.85 (4H, singlet), 4.20 − 3.86 (3H, multiplet), 0.77 (3H, doublet); TLC [chloroform-tetrahydrofuran-acetic acid (10:2:1)] Rf. = 0.20.
 b. 16-cyclopentyl-ω-trinor-trans-$\Delta^2$-$PGF_{1\alpha}$ 1.04 g. (1.9 mmole) of the carboxylic acid prepared as described in Example 15(b) gave 560 mg. (77.5%) of the title compound.

IR absorption spectrum (liquid film): 3330, 1700, 1642 and 970 cm$^{-1}$;

NMR spectrum (in CDCl$_3$): δ = 6.92 (1H, doublet-triplet), 5.80 (1H, doublet), 5.40 (2H, multiplet), 4.80 (4H, singlet), 4.20 – 3.85 (3H, multiplet), 0.87 (3H, doublet);

TLC [chloroform-tetrahydrofuran-acetic acid (10:2:1)] Rf. 0.12.

c. 15-methyl-trans-Δ$^2$-PGF$_{1α}$ 1.04 g. (1.95 mmole) of the carboxylic acid prepared as described in Example 15(c) gave 550 mg. (77.3%) of the title compound.

IR absorption spectrum (liquid film): 3330, 1697, 1642 and 960 cm$^{-1}$;

NMR spectrum (in CDCl$_3$): δ = 6.95 (1H, doublet-triplet), 5.80 (1H, doublet), 5.60 – 5.20 (2H, multiplet), 4.80 (4H, singlet), 4.06 (2H, multiplet);

TLC [chloroform-tetrahydrofuran-acetic acid (10:2:1)] Rf. = 0.21.

d. 15,16-dimethyl-trans-Δ$^2$-PGF$_{1α}$ 1.04 g. (1.9 mmole) of the carboxylic acid prepared as described in Example 15(d) gave 570 mg. (78.9%) of the title compound.

IR absorption spectrum (liquid film): 3340, 1698, 1643 and 980 cm$^{-1}$;

NMR spectrum (in CDCl$_3$): δ = 6.95 (1H, doublet-triplet), 5.80 (1H, doublet), 5.62 – 5.30 (2H, multiplet), 4.72 (4H, singlet), 4.05 (2H, multiplet);

TLC [chloroform-tetrahydrofuran-acetic acid (10:2:1)] Rf. = 0.22.

EXAMPLE 18

Synthesis of 16-phenyl-ω-trinor-trans-Δ$^2$-PGE$_1$ 834 mg. (1.5 mmole) of 9α-hydroxy-11α,15α-bis(2-tetrahydropyranyloxy)-16-phenyl-ω-trinor-prosta-trans-2,trans-13-dienoic acid (prepared as described in Example 14) were dissolved in diethyl ether, the solution was cooled in an ice-bath, and a solution of 5 g. of manganese sulphate, 1.03 g. of chromium trioxide, 1.15 g. of sulphuric acid and 23.9 ml. of water, was added; the reaction mixture was stirred at 0° - 5°C., for 2 hours. The reaction mixture was extracted with diethyl ether and the ethereal layer separated. The aqueous layer was saturated with sodium sulphate and extracted again with diethyl ether.

The combined extracts were washed with water, dried and concentrated under reduced pressure. The residue was purified by silica gel column chromatography using ethanol-benzene (6:94) as eluent to obtain 732 mg. (88%) of 9-oxo-11α,15α-bis(2-tetrahydropyranyloxy)-16-phenyl-ω-trinor-prosta-trans-2,trans-13-dienoic acid.

720 mg. (1.3 mmole) of the compound thus obtained were dissolved in a mixed solvent containing 11.8 ml. of acetic acid, 7.1 ml. of water and 1.42 ml. of tetrahydrofuran and stirred at 40°C. for 2 hours. The solution was added to 60 ml. of ice-water, the mixture extracted with ethyl acetate, and the combined extracts were washed with water, dried and concentrated under reduced pressure.

The residue was purified by silica gel column chromatography using cyclohexane-ethyl acetate (1:1) as eluent to yield 304 mg. (60%) of the title compound.

IR absorption spectrum (liquid film): 3400, 1737, 1700, 1655, 980 and 690 cm$^{-1}$;

NMR spectrum (in CDCl$_3$): δ = 7.20 (5H, multiplet), 6.92 (1H, doublet-triplet), 5.78 (1H, doublet), 5.60 (2H, multiplet), 4.80 (3H, singlet), 4.15 – 3.85 (2H, multiplet), 1.16 (3H, doublet);

TLC [chloroform-tetrahydrofuran-acetic acid (10:2:1)] Rf. = 0.27.

EXAMPLE 19

Using the procedure described in Example 18, the following compounds were obtained:

a. 16-cyclohexyl-ω-trinor-trans-Δ$^2$-PGE$_1$ 843 mg. (1.5 mmole) of 9α-hydroxy-11α,15α-bis(2-tetrahydropyranyloxy)-16-cyclohexyl-ω-trinor-prosta-trans-2,trans-13-dienoic acid prepared as described in Example 15(a) gave 310 mg. (52.6%) of the title compound.

IR absorption spectrum (liquid film): 3400, 1739, 1702, 1650, 980 and 902 cm$^{-1}$;

NMR spectrum (in CDCl$_3$): δ = 6.90 (1H, doublet-triplet), 5.79 (1H, doublet), 5.61 (2H, multiplet), 5.12 (3H, singlet), 4.09 (2H, multiplet), 2.76 (1H, doublet-doublet), 0.78 (3H, doublet);

TLC [chloroform-tetrahydrofuran-acetic acid (10:2:1)] Rf. = 0.31.

b. 16-cyclopentyl-ω-trinor-trans-Δ$^2$-PGE$_1$ 822 mg. (1.5 mmole) of 9α-hydroxy-11α,15α-bis(2-tetrahydropyranyloxy)-16-cyclopentyl-ω-trinor-prosta-trans-2,trans-13-dienoic acid prepared as described in Example 15(b) gave 296 mg. (52.2%) of the title compound.

IR absorption spectrum (liquid film): 3400, 1739, 1702, 1650 and 978 cm$^{-1}$;

NMR spectrum (in CDCl$_3$): δ = 6.90 (1H, doublet-triplet), 5.76 (1H, doublet), 5.61 (2H, multiplet), 5.00 (3H, singlet), 4.08 (2H, multiplet), 2.76 (1H, doublet-doublet), 0.88 (3H, doublet);

TLC [chloroform-tetrahydrofuran-acetic acid (10:2:1)] Rf. = 0.19.

c. 15-methyl-trans-Δ$^2$-PGE$_1$ 798 mg. (1.5 mmole) of 9α-hydroxy-11α,15-bis(2-tetrahydropyranyloxy)-15-methyl-prosta-trans-2,trans-13-dienoic acid prepared as described in Example 15(c) gave 297 mg. (53.0%) of the title compound.

IR absorption spectrum (liquid film): 3400, 1738, 1702, 1655 and 979 cm$^{-1}$;

NMR spectrum (in CDCl$_3$): δ = 6.92 (1H, doublet-triplet), 5.86 – 5.30 (3H, multiplet), 4.90 (3H, singlet), 4.09 (1H, multiplet), 2.74 (1H, doublet-doublet);

TLC [chloroform-tetrahydrofuran-acetic acid (10:2:1)] Rf. = 0.28.

d. 15,16-dimethyl-trans-Δ$^2$-PGE$_1$ 822 mg. (1.5 mmole) of 9α-hydroxy-11α,15-bis(2-tetrahydropyranyloxy)-15,16-dimethyl-prosta-trans-2,trans-13-dienoic acid prepared as described in Example 15(d) gave 296 mg. (52.1%) of the title compound.

IR absorption spectrum (liquid film): 3400, 1738, 1700, 1655 and 980 cm$^{-1}$;

NMR spectrum (in CDCl$_3$): δ = 6.92 (1H, doublet-triplet), 5.86 – 5.33 (3H, multiplet), 4.86 (3H, singlet), 4.08 (1H, multiplet), 2.73 (1H, doublet-doublet);

TLC [chloroform-tetrahydrofuran-acetic acid (10:2:1)] Rf. = 0.29.

EXAMPLE 20

Synthesis of 16-phenyl-ω-trinor-trans-Δ$^2$-PGA$_1$ 193 mg. (0.5 mmole) of 16-phenyl-ω-trinor-trans-Δ$^2$-PGE$_1$ (prepared as described in Example 18) were dissolved in 15 ml. of 90% acetic acid and stirred at 57° – 60°C., for 17 hours. The reaction mixture was concentrated under reduced pressure, the residue dissolved in diethyl ether, washed with water, dried and concentrated under reduced pressure.

The residue was purified by silica gel column chromatography using cyclohexane-ethyl acetate (4:1) as eluent to yield 116 mg. (63%) of the title compound.

IR absorption spectrum (liquid film): 3360, 3030, 2920, 1700 – 1680, 1590, 980 and 690 cm$^{-1}$;

NMR spectrum (in CDCl$_3$): δ = 7.46 (1H, doublet-doublet), 7.28 (5H, multiplet), 7.04 (1H, doublet-triplet), 6.42 (2H, singlet), 6.17 (1H, doublet-doublet), 5.82 (1H, doublet), 5.63 (2H, multiplet), 4.16 (1H, multiplet), 3.25 (1H, multiplet), 1.24 (3H, doublet);

TLC [chloroform-tetrahydrofuran-acetic acid (10:2:1)] Rf. = 0.72.

EXAMPLE 21

Using the procedure described in Example 20, the following compounds were obtained:

a. 16-cyclohexyl-ω-trinor-trans-Δ$^2$-PGA$_1$ 196 mg. (0.5 mmole) of 16-cyclohexyl-ω-trinor-trans-Δ$^2$-PGE$_1$ prepared as described in Example 19(a) gave 119 mg. (63.7%) of the title compound.

IR absorption spectrum (liquid film): 3370, 2900, 2840, 1700 – 1680, 1590, 975 and 902 cm$^{-1}$;

NMR spectrum (in CDCl$_3$): δ = 7.52 (1H, doublet-doublet), 7.04 (1H, doublet-triplet), 6.50 (2H, singlet), 6.20 (1H, doublet-doublet), 5.82 (1H, doublet), 5.62 (2H, multiplet), 4.10 (1H, multiplet), 3.28 (1H, multiplet), 0.77 (3H, doublet);

TLC [chloroform-tetrahydrofuran-acetic acid (10:2:1)] Rf. = 0.80.

b. 16-cyclopentyl-ω-trinor-trans-Δ$^2$-PGA$_1$ 189 mg. (0.5 mmole) of 16-cyclopentyl-ω-trinor-trans-Δ$^2$-PGE$_1$ prepared as described in Example 19(b) gave 113 mg. (62.8%) of the title compound.

IR absorption spectrum (liquid film): 3370, 2920, 2850, 1700 – 1680, 1590 and 978 cm$^{-1}$;

NMR spectrum (in CDCl$_3$): δ = 7.51 (1H, doublet-doublet), 7.04 (1H, doublet-triplet), 6.55 (2H, singlet), 6.20 (1H, doublet-doublet), 5.83 (1H, doublet), 5.61 (2H, multiplet), 4.11 (1H, multiplet), 3.27 (1H, multiplet), 0.87 (3H, doublet).

TLC [chloroform-tetrahydrofuran-acetic acid (10:2:1)] Rf. = 0.64.

c. 15-methyl-trans-Δ$^2$-PGA$_1$ 180 mg. (0.5 mmole) of 15-methyl-trans-Δ$^2$-PGE$_1$ prepared as described in Example 19(c) gave 109 mg. (63.7%) of the title compound.

IR absorption spectrum (liquid film): 3370, 2920, 2840, 1700 – 1680, 1590 and 978 cm$^{-1}$;

NMR spectrum (in CDCl$_3$): δ = 7.50 (1H, doublet-doublet), 7.03 (1H, doublet-triplet), 6.90 (2H, singlet), 6.16 (1H, doublet-doublet), 5.90 – 5.40 (3H, multiplet), 3.22 (1H, multiplet);

TLC [chloroform-tetrahydrofuran-acetic acid (10:2:1)] Rf. = 0.73.

d. 15,16-dimethyl-trans-Δ$^2$-PGA$_1$ 189 mg. (0.5 mmole) of 15,16-dimethyl-trans-Δ$^2$-PGE$_1$ prepared as described in Example 19(d) gave 110 mg. (61.2%) of the title compound.

IR absorption spectrum (liquid film): 3370, 2930, 2845, 1700 – 1680, 1590 and 980 cm$^{-1}$;

NMR spectrum (in CDCl$_3$): δ = 7.50 (1H, doublet-doublet), 7.03 (1H, doublet-triplet), 6.95 (2H, singlet), 6.16 (1H, doublet-doublet), 5.90 – 5.40 (3H, multiplet), 3.25 (1H, multiplet);

TLC [chloroform-tetrahydrofuran-acetic acid (10:2:1)] Rf. = 0.74.

REFERENCE EXAMPLE 18

Synthesis of dimethyl 2-oxo-4-ethylheptyl-phosphonate 120 g. of methyldimethyl phosphonate were dissolved in 800 ml. of anhydrous tetrahydrofuran and the solution cooled to −78°C. A solution of butyl lithium in diethyl ether, obtained from 200 g. of butyl bromide, 22 g. of lithium and 800 ml. of diethyl ether, was added at −45 to −50°C., and then a solution of 76 g. of sec-butyl-3-ethylhexanoate in 120 ml. of tetrahydrofuran was added at −60°C., and the reaction mixture stirred at this temperature for 2 hours and at room temperature for a further 3 hours. The reaction mixture was neutralised with acetic acid and concentrated under reduced pressure. The residue was dissolved in water, extracted with diethyl ether, and the ethereal layer was washed, dried and concentrated. The product thus obtained was distilled under reduced pressure to yield 68.4 g. of the title compound as a colourless oil, b.p. 115° to 124.5°C./0.4 to 0.5 mm.Hg.

IR absorption spectrum (liquid film): 2950, 2860, 1715, 1460, 1260, 1190, 1040 and 820 cm$^{-1}$.

REFERENCE EXAMPLE 19

Synthesis of 2-oxa-3-oxa-6-syn-(3-oxo-5-ethyl-oct-trans-1-enyl)-7-anti-acetoxy-cis-bicyclo[3,3,0]-octane 3.7 g. of sodium hydride (content 63.9%) were suspended in 700 ml. of anhydrous tetrahydrofuran and to this mixture a solution of 25 g. of dimethyl 2-oxo-4-ethylheptyl-phosphonate (prepared as described in Reference Example 18) in 100 ml. of tetrahydrofuran was added. During the addition hydrogen was vigorously evolved and the mixture became a clear yellow solution. A solution of 21 g. of 2-oxa-3-oxo-6-syn-formyl-7-anti-acetoxy-cis-bicyclo[3,3,0]octane (prepared as described in J. Amer. Chem. Soc. 92, 397 (1970) in 50 ml. of tetrahydrofuran was added and the reaction mixture stirred at room temperature for one hour; 7 g. of acetic acid were added to stop the reaction. The resulting precipitate was filtered off and the filtrate was concentrated under reduced pressure. The residue was purified by column chromatography on silica gel using ethyl acetate - benzene (1:7) as eluent to obtain 21.5 g. (64%) of the title compound as a light yellow oil.

IR absorption spectrum (liquid film): 2950, 2850, 1775, 1740, 1690, 1660, 1625, 1455, 1370, 1240, 1170, 1070 and 980 cm$^{-1}$;

NMR spectrum (in CDCl$_3$): δ = 6.78 (1H, quartet), 6.23 (1H, doublet), 5.25 – 4.86 (2H, multiplet), 2.04 (3H, singlet) and 0.9 (6H, triplet);

TLC [benzene - methanol - diethyl ether (5:1:1)] Rf.=0.71.

REFERENCE EXAMPLE 20

Synthesis of 2-oxa-3-oxo-6-syn-(3-hydroxy-5-ethyl-oct-trans-1-enyl)-7-anti-acetoxy-cis-bicyclo[3,3,0]-octane 38.5 g. of 2-oxa-3-oxo-6-syn-(3-oxo-5-ethyl-oct-trans-1-enyl)-7-anti-acetoxy-cis-bicyclo[3,3,0]-octane (prepared as described in Reference Example 19) were dissolved in 370 ml. of methanol, and to this solution were added 13 g. of sodium borohydride after cooling to −30° to −40°C. The reaction mixture was stirred for 15 minutes, neutralised with acetic acid and concentrated under reduced pressure. The residue was dissolved in ethyl acetate, washed with a saturated solution of sodium bicarbonate and brine, dried and concentrated under reduced pressure to obtain 38.6 g. (99.7%) of the title compound as a light yellow oil.

IR absorption spectrum (liquid film): 3460, 2960 – 2870, 1770, 1740, 1460, 1420, 1375, 1240, 1180, 1075, 1060 and 975 cm$^{-1}$;

NMR spectrum (in CDCl$_3$): $\delta$ = 5.55 (2H, multiplet), 5.02 – 4.6 (3H, multiplet), 4.15 – 3.75 (3H, multiplet), 1.92 (3H, singlet) and 1.0 – 0.8 (6H, triplet);

TLC ]methylene chloride - methanol (20:1)]Rf. = 0.39.

REFERENCE EXAMPLE 21

Synthesis of 2-oxa-3-hydroxy-6-syn-(3-2'-tetrahydropyranyloxy-5-ethyl-oct-trans-1-enyl)-7-anti-(2-tetrahydropyranyloxy)-cis-bicyclo-[3,3,0]-octane 11.5 g. of 2-oxa-3-oxo-6-syn-(3-hydroxy-5-ethyl-oct-trans-1-enyl)-7-anti-acetoxy-cis-bicyclo-[3,3,0]-octane (prepared as described in Reference Example 20) were stirred with an equimolar amount of potassium carbonate in absolute methanol at 25°C., for 30 minutes to obtain 10 g. (99%) of the diol as a light yellow oil. TLC [methylene chloride - methanol (20:1)] Rf. = 0.24.

The diol obtained (9.6 g.) was dissolved in 100 ml. of methylene chloride, 100 mg. of p-toluene sulphonic acid and 11 ml. of dihydropyran were added and the solution stirred at room temperature for 15 minutes to obtain 15.6 g. (100%) of the bis-tetrahydropyranyl ether as a light yellow oil.

TLC [methylene chloride - methanol (20:1)] Rf. = 0.79.

The bis-tetrahydropyranyl ether (15.2 g.) was dissolved in 400 ml. of toluene, cooled to −60°C., and two equivalents of diisobutylaluminium hydride in toluene were added with stirring and the stirring continued for 30 minutes to obtain 15.3 g. (100%) of the title compound as a light yellow oil.

IR absorption spectrum (liquid film): 3430, 2950, 2870, 1670, 1450, 1380, 1360, 1260, 1200, 1190, 1130, 1080, 1020, 980, 920, 875 and 820 cm$^{-1}$;

NMR spectrum (in CDCl$_3$): $\delta$ = 5.7 – 5.15 (2H, multiplet), 4.85 – 4.25 (3H, multiplet), 4.2 – 3.15 (8H, multiplet) and 1.0 – 0.8 (6H, triplet);

TLC [methylene chloride - methanol (20:1) Rf. = 0.39.

REFERENCE EXAMPLE 22

Synthesis of 9$\alpha$-hydroxy-11$\alpha$,15-bis(2-tetrahydropyranyloxy)-17-ethyl-$\alpha$-dinor-prost-trans-13-enoic acid.

Proceeding as described in Reference Example 8 using 53 g. (0.127 mole) of 2-carboxyethyltriphenylphosphonium bromide and 20.4 g. of 2-oxa-3-hydroxy-6-syn-(3-2'-tetrahydropyranyloxy-5-ethyl-oct-trans-1-enyl)-7-anti-(2-tetrahydropyranyloxy)-cis-bicy-clo[3,3,0]-octane (prepared as described in Reference Example 21), there were obtained 13.0 g. (57%) of 9$\alpha$-hydroxy-11$\alpha$,15-bis(2-tetrahydropyranyloxy)-17-ethyl-$\alpha$-dinor-prosta-cis-5, trans-13-dienoic acid as a light yellow oil.

IR absorption spectrum (liquid film): 3430, 2940, 1710, 1450, 1380, 1245, 1135, 1025, 980 and 870 cm$^{-1}$;

NMR spectrum (in CDCl$_3$): $\delta$ = 7.00 (2H, singlet), 5.67 – 5.20 (4H, multiplet) and 4.65 (2H, multiplet).

Proceeding as described in Reference Example 8 the resulting compound was hydrogenated using as catalyst 5% palladium on charcoal to obtain 9.75 g. (75%) of the title compound.

REFERENCE EXAMPLE 23

Synthesis of methyl 9$\alpha$-hydroxy-11$\alpha$,15-bis(2-tetrahydropyranyloxy)-17-ethyl-$\alpha$-dinor-prost-trans-13-enoate Proceeding as described in Reference Example 9 using 9.45 g. of 9$\alpha$-hydroxy-11$\alpha$,15-bis(2-tetrahydropyranyloxy)-17-ethyl-$\alpha$-dinor-prost-trans-13-enoic acid (prepared as described in Reference Example 22), 8.2 g. of the title compound were obtained as a colourless oil.

IR absorption spectrum (liquid film): 3450, 2930, 1740, 1445, 1025 and 680 cm$^{-1}$;

NMR spectrum (in CDCl$_3$): $\delta$ = 5.65 – 5.26 (2H, multiplet), 4.70 (2H, multiplet), 3.62 (3H, singlet and 4.24 – 3.2 (7H, multiplet);

TLC [methylene chloride - methanol (19:1)] Rf. = 0.64.

REFERENCE EXAMPLE 24

Synthesis of 9$\alpha$-hydroxy-11$\alpha$,15-bis(2-tetrahydropyranyloxy)-17-ethyl-$\alpha$-dinor-prost-trans-13-enaldehyde Proceeding as described in Reference Example 10 using 7.76 g. of methyl 9$\alpha$-hydroxy-11$\alpha$,15-bis(2-tetrahydropyranyloxy)-17-ethyl-$\alpha$-dinor-prost-trans-13-enoate (prepared as described in Reference Example 23), 6.12 g. (97%) of the title compound were obtained.

TLC [cyclohexane - ethyl acetate (1:1)]Rf. = 0.54.

EXAMPLE 22

Synthesis of ethyl 9$\alpha$-hydroxy-11$\alpha$,15-bis(2-tetrahydropyranyloxy)-17-ethyl-prosta-trans-2,trans-13-dienoate To a mixture of 4.71 g. (content 63.9%; 37.5 mmole) of sodium hydride and 150 ml. of tetrahydrofuran, 8.43 g. (37.5 mmole) of triethylphosphonoacetate was added dropwise keeping the temperature below 30°C., and the reaction mixture was stirred at 25°C., for about 30 minutes until the evolution of hydrogen ceased.

A solution of 5.46 g. (10.74 mmole) of the aldehyde, prepared as described in Reference Example 24, in 180 ml. of tetrahydrofuran was added to the reaction mixture and stirred at 25°C., for 45 minutes. The solution was adjusted to pH 7 with acetic acid, diluted with water and extracted with diethyl ether. The ethereal layer was washed with water, dried and concentrated. The residue was purified by column chromatography on silica gel using ethyl acetate - cyclohexane (1:3) as eluent to yield 4.52 g. (73%) of the title compound.

IR absorption spectrum (liquid film): 3450, 2950, 1720, 1650, 1025 cm$^{-1}$;

NMR spectrum (in CDCl$_3$): $\delta$ = 6.87 (1H, doublet-triplet), 5.68 (1H, doublet), 5.71 – 5.27 (2H, multiplet, 4.63 (2H, multiplet, 4.09 (2H, quartet) and 4.10 – 3.30 (7H, multiplet);

TLC [cyclohexane - ethyl acetate (1:1)] Rf. = 0.68.

EXAMPLE 23

Synthesis of
9α-hydroxy-11α,15-bis(2-tetrahydropyranyloxy)-17-ethyl-prosta-trans-2,trans-13-dienoic acid 4.50 g. of the ethyl ester prepared as described in Example 22 were dissolved in 45 ml. of tetrahydrofuran; an aqueous solution of 4.27 g. of potassium hydroxide was added and the mixture stirred at 25°C., for 2 hours.

The reaction mixture was diluted with 150 ml. of water, acidified to pH 5 with oxalic acid, 150 ml. of water added and the solution extracted four times with 250 ml. of ethyl acetate. The organic layer was washed with water, dried and concentrated under reduced pressure. The residue was purified by column chromatography on silica gel using benzene - ethyl acetate (3:1) as eluent to yield 3.13 g. (73%) of the title compound.

IR absorption spectrum (liquid film): 3400, 2940, 2840, 1700, 1640, 1120, 1020 and 980 cm$^{-1}$;

NMR spectrum (in CDCl$_3$): $\delta$ = 6.90 (1H, doublet-triplet), 6.25 (2H, singlet), 5.75 (1H, doublet), 5.54 − 5.20 (2H, multiplet), 4.62 (2H, multiplet), 4.12 − 3.20 (7H, multiplet);

TLC [methylene chloride - methanol (19:1)] Rf. = 0.26.

EXAMPLE 24

Synthesis of 17-ethyl-trans-$\Delta^2$-PGF$_{1\alpha}$ and 17-ethyl-trans-$\Delta^2$-15-epi-PGF$_{1\alpha}$ 1.06 g. of the bis-tetrahydropyranyl ether prepared as described in Example 23 were dissolved in 120 ml. of a mixture of N hydrochloric acid and tetrahydrofuran (1:1) and the solution stirred at room temperature for one hour. The reaction mixture was poured into 300 ml. of ice-water, extracted with ethyl acetate, and the organic layer was washed with water, dried and concentrated under reduced pressure. The residue was separated by column chromatography on silica gel using ethyl acetate - cyclohexane (5:1) as eluent to yield 245 mg. of 17-ethyl-trans-$\Delta^2$-PGF$_{1\alpha}$ and 232 mg. of 17-ethyl-trans-$\Delta^2$-15-epi-PGF$_{1\alpha}$ (total yield 66%).

IR absorption spectrum (liquid film) each of them: 3350, 1700, 1640 and 965 cm$^{-1}$;

NMR spectrum (in CDCl$_3$) and each of them: $\delta$ = 6.90 (1H, doublet-triplet), 5.78 (1H, doublet), 5.62 − 5.22 (2H multiplet), 4.90 (4H, singlet) and 4.05 (3H, multiplet);

TLC [chloroform- tetrahydrofuran - acetic acid (10:2:1)] 17-ethyl-trans-$\Delta^2$-PGF$_{1\alpha}$ : Rf. = 0.21; 17-ethyl-trans-$\Delta^2$-15-epi-PGF$_{1\alpha}$ : Rf. = 0.24.

EXAMPLE 25

Synthesis of 17-ethyl-trans-$\Delta^2$-PGE$_1$ and 17-ethyl-trans-$\Delta^2$-15-epi-PGE$_1$ Proceeding as described in Example 6 using 2.11 g. of 9α-hydroxy-11α,15-bis(2-tetrahydropyranyloxy)-17-ethyl-prosta-trans-2,trans-13-dienoic acid (prepared as described in Example 23) and with separation of the product by column chromatography on silica gel as described in Example 24, 350 mg. of 17-ethyl-trans-$\Delta^2$-PGE$_1$ and 337 mg. of 17-ethyl-trans-$\Delta^2$-15-epi-PGE$_1$ (total yield: 47%) were obtained.

IR absorption spectrum (liquid film) each of them: 3400, 2700 − 2300, 1705, 1645, 1450, 1380, 1240, 1080 and 980 cm$^{-1}$;

NMR spectrum (in CDCl$_3$) each of them: $\delta$ = 6.96 (1H, doublet-triplet), 5.84 (1H, doublet), 5.68 − 5.30 (5H, multiplet), 4.23 − 3.81 (2H, multiplet) and 2.75 (1H, doublet-doublet);

TLC [chloroform - tetrahydrofuran - acetic acid (10:2:1)] 17-ethyl-trans-$\Delta^2$-PGE$_1$: Rf. = 0.27 17-ethyl-trans-$\Delta^2$-15-epi-PGE$_1$: Rf. = 0.29.

EXAMPLE 26

Synthesis of 17-ethyl-trans-$\Delta^2$-PGA$_1$

Proceeding as described in Example 7 using 350 mg. of 17-ethyl-trans-$\Delta^2$-PGE$_1$, (prepared as described in Example 25), 210 mg. of 17ethyl-trans-$\Delta^2$-PGA$_1$ were obtained.

IR absorption spectrum (liquid film): 3400, 2950 − 2300, 1710, 1660, 1595, 1460 and 980 cm$^{-1}$;

NMR spectrum (in CDCl$_3$): $\delta$ = 7.48 (1H, doublet-doublet), 7.00 (1H, doublet-triplet), 6.18 (1H, doublet-doublet), 5.87 − 5.43 (5H, multiplet) and 3.98 (1H, multiplet);

TLC [chloroform -tetrahydrofuran - acetic acid (10:2:1)] Rf. = 0.68.

In the foregoing Examples and compounds mentioned in the accompanying claims where the configuration of a radical or group is unspecified, it is to be understood that in the case of tetrahydropyranyloxy groups the configuration is α or β or a mixture of α- and β- configurations, or in the case of alkyl radicals or phenyl or cycloalkyl radicals the configuration is R or S or a mixture of R- and S- configurations.

The present invention includes within its scope pharmaceutical compositions which comprise at least one new therapeutically useful prostaglandin compound according to the present invention, together with a pharmaceutical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.01 and 5 mg/kg. body weight by oral administration in the treatment of hypertension, between 0.5 and 100 $\mu$g./kg. body weight by oral administration in the treatment of gastric ulceration, between 0.1 and 50 $\mu$g./kg. body weight by aerosol administration in the treatment of astham, between 0.01 and 5 mg./kg. body weight by oral administration in the treatment of disorders of the peripheral circulation and between 0.01 and 5 mg./kg. body weight by oral administration in the prevention and treatment of cerebral thrombosis and myocardial infarction.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which disperses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg., of active ingredient per ml. of solution or suspension. It is important that the pH of solutions and suspensions used, according to the present invention, to generate aerosols should be kept within the range 3° to 8° and preferable that they should be stored at or below 4°C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is be means of devices enabling controlled quantities of the active ingredients to be administered, for example by means of the metered valves hereinbefore mentioned.

The following Examples illustrates pharmaceutical compositions according to the invention.

EXAMPLE 27

16(R)-methyl-trans-$\Delta^2$PGE$_1$ (500 $\mu$g.) was dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 50 $\mu$g. of 16(R)-methyl-trans-$\Delta^2$-PGE$_1$ (in the form of its sodium salt) per ampoule. The contents of the ampoules were freeze-dried and the ampoules sealed. The contents of an ampoule in a suitable volume, e.g. 2 ml., of sterile water of physiological saline gave a solution ready for administration by injection.

EXAMPLE 28

16(R)-methyl-trans-$\Delta^2$-PGE$_1$ (20 mg.) was dissolved in ethanol (10 ml.), mixed with mannitol (18.5 g.), sieved through a 30-mesh sieve, dried at 30°C. for 90 minutes and again sieved through a 30-mesh sieve. Aerosil (microfine silica; 200 mg.) was added and the powder obtained was machine-filled into one hundred No. 2 hard gelatin capsules to give capsules each containing 200 $\mu$g. of 16(R)-methyl-trans-$\Delta^2$-PGE$_1$, which after swallowing of the capsule is released into the stomach.

We claim:

1. A compound of the formula:

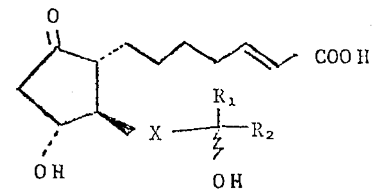

in which X is $-CH_2CH_2-$ or trans $-CH{=}CH-$, R$_1$ is a branched-chain alkyl radical of 1 to 10 carbon atoms or a straight- or branched-chain alkyl radical of 1 to 6 carbon atoms substituted by phenyl or cycloalkyl of 5 to 7 carbon atoms and R$_2$ is hydrogen or a straight- or branched-chain alkyl radical of 1 to 4 carbon atoms, and in which ∿ indicates attachment of the hydroxyl radical to the carbon atom in alpha or beta configuration, and the corresponding cyclodextrin clathrates, alkyl esters and non-toxic salts thereof.

2. A compound according to claim 1 which is trans-$\Delta^2$-dihydro-PGE$_1$.

3. A compound according to claim 1 which is 16(R)-methyl-trans-$\Delta^2$-PGE$_1$.

4. A compound according to claim 1 which is 17-methyl-trans-$\Delta^2$-PGE$_1$.

5. A compound according to claim 1 which is 16-phenyl-ω-trinor-trans-$\Delta^2$-PGE$_1$.

6. A compound according to claim 1 which is 16-cyclohexyl-ω-trinor-trans-$\Delta^2$-PGE$_1$.

7. A compound according to claim 1 which is 16-cyclopentyl-ω-trinor-trans-$\Delta^2$-PGE$_1$.

8. A compound according to claim 1 which is 15,16-dimethyl-trans-$\Delta^2$-PGE$_1$.

9. A compound according to claim 1 which is 17-ethyl-trans-$\Delta^2$-PGE$_1$.

10. A compound according to claim 1 which is 17-ethyl-trans-$\Delta^2$-15-epi-PGE$_1$.

11. A compound which is 15-methyl-trans-$\Delta^2$-PGE$_1$.

* * * * *